(12) United States Patent
Levine et al.

(10) Patent No.: US 7,758,535 B2
(45) Date of Patent: *Jul. 20, 2010

(54) BARIATRIC SLEEVE DELIVERY DEVICES

(75) Inventors: Andy H. Levine, Newton, MA (US);
Dave Melanson, Hudson, NH (US)

(73) Assignee: GI Dynamics, Inc., Lexington, MA (US)

( * ) Notice: Subject to any disclaimer, the term of this patent is extended or adjusted under 35 U.S.C. 154(b) by 26 days.

This patent is subject to a terminal disclaimer.

(21) Appl. No.: 12/001,365

(22) Filed: Dec. 11, 2007

(65) Prior Publication Data

US 2008/0097466 A1 Apr. 24, 2008

Related U.S. Application Data

(60) Continuation-in-part of application No. 10/999,846, filed on Nov. 30, 2004, now Pat. No. 7,329,285, which is a division of application No. 10/339,786, filed on Jan. 9, 2003, now Pat. No. 7,025,791.

(60) Provisional application No. 60/430,321, filed on Dec. 2, 2002.

(51) Int. Cl.
*A61M 5/00* (2006.01)
(52) U.S. Cl. .......................... 604/8; 606/108; 606/151; 623/23.64; 623/23.68
(58) Field of Classification Search .................. 604/8; 623/23.64, 23.65, 23.66, 23.68; 606/108, 606/151, 191; 600/37
See application file for complete search history.

(56) References Cited

U.S. PATENT DOCUMENTS

| 1,899,781 | A | 2/1933 | Twiss |
| 2,464,933 | A | 3/1949 | Kaslow |
| 3,516,408 | A | 6/1970 | Montanti |
| 3,780,740 | A | 12/1973 | Rhea |
| 4,133,315 | A | 1/1979 | Berman et al. |
| 4,134,405 | A | 1/1979 | Smit |
| 4,246,893 | A | 1/1981 | Berson |

(Continued)

FOREIGN PATENT DOCUMENTS

DE 33 26 061 A1 2/1984

(Continued)

OTHER PUBLICATIONS

Bethge, N., et al., "Human Tissue Responses to Metal Stents Implanted in vivo for the Palliation of Malignant Stenoses," *Gastrointestinal Endoscopy*, 43(6):596-602 (Jun. 1996).

(Continued)

*Primary Examiner*—Alvin J Stewart
(74) *Attorney, Agent, or Firm*—Hamilton, Brook, Smith & Reynolds, P.C.

(57) ABSTRACT

Method and apparatus for limiting absorption of food products in specific parts of the digestive system is presented. A gastrointestinal implant device is anchored in the stomach and extends beyond the ligament of Treitz. All food exiting the stomach is funneled through the device. The gastrointestinal device includes an anchor for anchoring the device to the stomach and a flexible sleeve to limit absorption of nutrients in the duodenum. The anchor is collapsible for endoscopic delivery and removal.

34 Claims, 30 Drawing Sheets

U.S. PATENT DOCUMENTS

| | | |
|---|---|---|
| 4,265,694 A | 5/1981 | Boretos et al. |
| 4,270,542 A | 6/1981 | Plumley |
| 4,271,827 A | 6/1981 | Angelchik |
| 4,279,251 A | 7/1981 | Rüsch |
| 4,315,509 A | 2/1982 | Smit |
| 4,341,218 A | 7/1982 | U |
| 4,403,604 A | 9/1983 | Wilkinson et al. |
| 4,416,267 A | 11/1983 | Garren et al. |
| 4,501,264 A | 2/1985 | Rockey |
| 4,580,568 A | 4/1986 | Gianturco |
| 4,607,618 A | 8/1986 | Angelchik |
| 4,617,932 A | 10/1986 | Kornberg |
| 4,641,653 A | 2/1987 | Rockey |
| 4,648,383 A | 3/1987 | Angelchik |
| 4,763,653 A | 8/1988 | Rockey |
| 4,768,507 A | 9/1988 | Fischell et al. |
| 4,823,808 A | 4/1989 | Clegg et al. |
| 4,846,836 A | 7/1989 | Reich |
| 4,878,905 A | 11/1989 | Blass |
| 4,905,693 A | 3/1990 | Ravo |
| 4,913,141 A | 4/1990 | Hillstead |
| 4,991,594 A | 2/1991 | Angelchik |
| 4,994,070 A | 2/1991 | Waters |
| 5,035,706 A | 7/1991 | Gianturco et al. |
| 5,037,387 A | 8/1991 | Quinn et al. |
| 5,041,126 A | 8/1991 | Gianturco |
| 5,057,091 A | 10/1991 | Andersen |
| 5,059,166 A | 10/1991 | Fischell et al. |
| 5,104,399 A | 4/1992 | Lazarus |
| 5,123,917 A | 6/1992 | Lee |
| 5,135,516 A | 8/1992 | Sahatjian et al. |
| 5,152,756 A * | 10/1992 | Quinn et al. ............... 604/270 |
| 5,152,782 A | 10/1992 | Kowligi et al. |
| 5,176,617 A | 1/1993 | Fischell et al. |
| 5,190,561 A | 3/1993 | Graber |
| 5,234,454 A | 8/1993 | Bangs |
| 5,236,423 A | 8/1993 | Mix et al. |
| 5,246,456 A | 9/1993 | Wilkinson |
| 5,254,133 A | 10/1993 | Seid |
| 5,279,553 A | 1/1994 | Winkler et al. |
| 5,282,824 A | 2/1994 | Gianturco |
| 5,290,294 A | 3/1994 | Cox et al. |
| 5,306,300 A | 4/1994 | Berry |
| 5,314,444 A | 5/1994 | Gianturco |
| 5,314,472 A | 5/1994 | Fontaine |
| 5,314,473 A | 5/1994 | Godin |
| 5,318,530 A | 6/1994 | Nelson, Jr. |
| 5,322,501 A | 6/1994 | Mahmud-Durrani |
| 5,330,500 A | 7/1994 | Song |
| 5,364,353 A | 11/1994 | Corfitsen et al. |
| 5,387,235 A | 2/1995 | Chuter |
| 5,389,090 A | 2/1995 | Fischell et al. |
| 5,401,241 A | 3/1995 | Delany |
| 5,405,378 A | 4/1995 | Strecker |
| 5,417,697 A | 5/1995 | Wilk et al. |
| 5,423,851 A | 6/1995 | Samuels |
| 5,443,498 A | 8/1995 | Fontaine |
| 5,456,713 A | 10/1995 | Chuter |
| 5,458,605 A * | 10/1995 | Klemm ............... 606/108 |
| 5,458,615 A | 10/1995 | Klemm et al. |
| 5,480,423 A | 1/1996 | Ravenscroft et al. |
| 5,492,530 A | 2/1996 | Fischell et al. |
| 5,507,767 A | 4/1996 | Maeda et al. |
| 5,507,771 A | 4/1996 | Gianturco |
| 5,522,880 A | 6/1996 | Barone et al. |
| 5,562,697 A | 10/1996 | Christiansen |
| 5,569,219 A | 10/1996 | Hakki et al. |
| 5,571,173 A | 11/1996 | Parodi |
| 5,605,530 A | 2/1997 | Fischell et al. |
| 5,607,442 A | 3/1997 | Fischell et al. |
| 5,611,787 A | 3/1997 | Demeter et al. |
| 5,620,763 A | 4/1997 | House et al. |
| 5,624,430 A | 4/1997 | Eton et al. |
| 5,630,797 A | 5/1997 | Diedrich et al. |
| 5,634,928 A | 6/1997 | Fischell et al. |
| 5,639,274 A | 6/1997 | Fischell et al. |
| 5,643,312 A | 7/1997 | Fischell et al. |
| 5,662,713 A | 9/1997 | Andersen et al. |
| 5,665,064 A | 9/1997 | Bodicky et al. |
| 5,669,932 A | 9/1997 | Fischell et al. |
| 5,690,642 A | 11/1997 | Osborne et al. |
| 5,693,084 A | 12/1997 | Chuter |
| 5,695,516 A | 12/1997 | Fischell et al. |
| 5,697,971 A | 12/1997 | Fischell et al. |
| 5,713,948 A | 2/1998 | Uflacker |
| 5,715,832 A | 2/1998 | Koblish et al. |
| 5,718,973 A | 2/1998 | Lewis et al. |
| 5,720,776 A | 2/1998 | Chuter et al. |
| 5,722,984 A | 3/1998 | Fischell et al. |
| 5,730,698 A | 3/1998 | Fischell et al. |
| 5,733,325 A | 3/1998 | Robinson et al. |
| 5,735,859 A | 4/1998 | Fischell et al. |
| 5,735,892 A | 4/1998 | Myers et al. |
| 5,743,874 A | 4/1998 | Fischell et al. |
| 5,749,825 A | 5/1998 | Fischell et al. |
| 5,755,777 A | 5/1998 | Chuter |
| 5,759,174 A | 6/1998 | Fischell et al. |
| 5,776,186 A | 7/1998 | Uflacker |
| 5,792,144 A | 8/1998 | Fischell et al. |
| 5,792,172 A | 8/1998 | Fischell et al. |
| 5,800,456 A | 9/1998 | Maeda et al. |
| 5,800,526 A | 9/1998 | Anderson et al. |
| 5,820,584 A | 10/1998 | Crabb |
| 5,830,229 A | 11/1998 | Konya et al. |
| 5,840,009 A | 11/1998 | Fischell et al. |
| 5,843,164 A | 12/1998 | Frantzen et al. |
| 5,855,601 A | 1/1999 | Bessler et al. |
| 5,876,445 A | 3/1999 | Andersen et al. |
| 5,879,282 A | 3/1999 | Fischell et al. |
| 5,879,370 A | 3/1999 | Fischell et al. |
| 5,895,391 A | 4/1999 | Farnholtz |
| 5,910,145 A | 6/1999 | Fischell et al. |
| 5,913,895 A | 6/1999 | Burpee et al. |
| 5,919,233 A | 7/1999 | Knopf et al. |
| 5,925,063 A | 7/1999 | Khosravi |
| 5,962,620 A | 10/1999 | Reich et al. |
| 5,963,620 A | 10/1999 | Frankel et al. |
| 5,976,153 A | 11/1999 | Fischell et al. |
| 5,964,771 A | 12/1999 | Beyar et al. |
| 6,013,019 A | 1/2000 | Fischell et al. |
| 6,013,085 A * | 1/2000 | Howard ............... 606/108 |
| 6,025,044 A | 2/2000 | Campbell et al. |
| 6,027,508 A | 2/2000 | Ren et al. |
| 6,027,526 A | 2/2000 | Limon et al. |
| 6,035,856 A | 3/2000 | LaFontaine et al. |
| 6,074,673 A | 6/2000 | Guillen |
| 6,086,604 A | 7/2000 | Fischell et al. |
| 6,099,552 A | 8/2000 | Adams |
| 6,102,887 A | 8/2000 | Altman |
| 6,113,607 A * | 9/2000 | Lau et al. ............... 606/108 |
| 6,120,533 A | 9/2000 | Fischell |
| 6,120,534 A | 9/2000 | Ruiz |
| 6,132,471 A | 10/2000 | Johlin, Jr. |
| 6,146,323 A | 11/2000 | Fischell |
| 6,152,956 A | 11/2000 | Pierce |
| 6,179,868 B1 | 1/2001 | Burpee et al. |
| 6,187,016 B1 | 2/2001 | Hedges et al. |
| 6,190,403 B1 | 2/2001 | Fischell et al. |
| 6,200,336 B1 | 3/2001 | Pavcnik et al. |
| 6,221,043 B1 | 4/2001 | Fischell et al. |
| 6,221,102 B1 | 4/2001 | Baker et al. |
| 6,241,738 B1 | 6/2001 | Dereume |
| 6,241,757 B1 | 6/2001 | An et al. |
| 6,251,064 B1 | 6/2001 | Silverman et al. |

| | | | | | |
|---|---|---|---|---|---|
| 6,251,132 B1 | 6/2001 | Ravenscroft et al. | 7,037,344 B2 | 5/2006 | Kagan et al. |
| 6,270,521 B1 | 8/2001 | Fischell et al. | 7,081,132 B2 | 7/2006 | Cook et al. |
| 6,293,960 B1 | 9/2001 | Ken | 7,087,088 B2 | 8/2006 | Berg et al. |
| 6,302,891 B1 | 10/2001 | Nadal | 7,121,283 B2 | 10/2006 | Stack et al. |
| 6,302,917 B1 | 10/2001 | Dua et al. | 7,122,058 B2 * | 10/2006 | Levine et al. ............ 623/23.65 |
| 6,315,708 B1 | 11/2001 | Salmon et al. | 7,146,984 B2 | 12/2006 | Stack et al. |
| 6,322,538 B1 | 11/2001 | Elbert et al. | 7,152,607 B2 | 12/2006 | Stack et al. |
| 6,331,190 B1 | 12/2001 | Shokoohi et al. | 7,160,312 B2 | 1/2007 | Saadat |
| 6,332,877 B1 | 12/2001 | Michels | 7,211,114 B2 | 5/2007 | Bessler et al. |
| 6,355,056 B1 | 3/2002 | Pinheiro | 7,220,237 B2 | 5/2007 | Gannoe et al. |
| 6,356,782 B1 | 3/2002 | Sirimanne et al. | 7,220,284 B2 | 5/2007 | Kagan et al. |
| 6,375,660 B1 | 4/2002 | Fischell et al. | 7,267,694 B2 | 9/2007 | Levine et al. |
| 6,383,214 B1 | 5/2002 | Banas et al. | 7,314,489 B2 | 1/2008 | McKenna et al. |
| 6,387,114 B2 | 5/2002 | Adams | 7,329,285 B2 | 2/2008 | Levine et al. |
| 6,402,779 B1 | 6/2002 | Colone et al. | 7,338,520 B2 | 3/2008 | Bailey et al. |
| 6,406,792 B1 | 6/2002 | Briquet et al. | 7,347,875 B2 | 3/2008 | Levine et al. |
| 6,401,718 B1 | 7/2002 | Johnson et al. | 7,354,454 B2 | 4/2008 | Stack et al. |
| 6,428,558 B1 | 8/2002 | Jones et al. | 7,476,256 B2 | 1/2009 | Meade et al. |
| 6,450,989 B2 | 9/2002 | Dubrul et al. | 7,507,218 B2 | 3/2009 | Aliski et al. |
| 6,458,074 B1 | 10/2002 | Matsui et al. | 7,513,914 B2 | 4/2009 | Schurr |
| 6,485,409 B1 | 11/2002 | Voloshin et al. | 7,621,886 B2 | 11/2009 | Burnett |
| 6,485,515 B2 | 11/2002 | Strecker | 2001/0020190 A1 | 9/2001 | Taylor |
| 6,508,833 B1 | 1/2003 | Pavcnik et al. | 2002/0022853 A1 | 2/2002 | Swanson et al. |
| 6,520,985 B1 | 2/2003 | Burpee et al. | 2002/0032487 A1 | 3/2002 | Dua et al. |
| 6,524,268 B2 | 2/2003 | Hayner et al. | 2002/0065545 A1 | 5/2002 | Leonhardt et al. |
| 6,524,335 B1 | 2/2003 | Hartley et al. | 2002/0091439 A1 | 7/2002 | Baker et al. |
| 6,524,336 B1 | 2/2003 | Papazolgou et al. | 2002/0120277 A1 | 8/2002 | Hauschild et al. |
| 6,530,951 B1 | 3/2003 | Bates et al. | 2002/0143387 A1 | 10/2002 | Soetikno et al. |
| 6,537,247 B2 | 3/2003 | Shannon | 2002/0147489 A1 | 10/2002 | Hong et al. |
| 6,540,775 B1 | 4/2003 | Fischell et al. | 2002/0151953 A1 | 10/2002 | Chobotov et al. |
| 6,540,789 B1 | 4/2003 | Silverman et al. | 2002/0177890 A1 | 11/2002 | Lenker |
| 6,544,291 B2 | 4/2003 | Taylor | 2002/0183768 A1 | 12/2002 | Deem et al. |
| 6,547,817 B1 | 4/2003 | Fischell et al. | 2002/0183786 A1 | 12/2002 | Girton |
| 6,558,400 B2 | 5/2003 | Deem et al. | 2002/0188344 A1 | 12/2002 | Bolea et al. |
| 6,558,429 B2 | 5/2003 | Taylor | 2002/0193828 A1 | 12/2002 | Griffin et al. |
| 6,565,597 B1 | 5/2003 | Fearnot et al. | 2003/0032941 A1 | 2/2003 | Boyle et al. |
| 6,572,646 B1 * | 6/2003 | Boylan et al. ............... 623/1.12 | 2003/0040804 A1 | 2/2003 | Stack et al. |
| 6,589,213 B2 | 7/2003 | Reydel | 2003/0040808 A1 | 2/2003 | Stack et al. |
| 6,589,275 B1 | 7/2003 | Ivancev et al. | 2003/0050684 A1 | 3/2003 | Abrams et al. |
| 6,623,518 B2 | 9/2003 | Thompson et al. | 2003/0069539 A1 | 4/2003 | Gandhi et al. |
| 6,635,069 B1 | 10/2003 | Teoh et al. | 2003/0109892 A1 | 6/2003 | Deem et al. |
| 6,635,079 B2 | 10/2003 | Unsworth et al. | 2003/0109931 A1 | 6/2003 | Geitz |
| 6,645,239 B1 | 11/2003 | Park et al. | 2003/0109935 A1 | 6/2003 | Geitz |
| 6,652,555 B1 | 11/2003 | VanTassel et al. | 2003/0120265 A1 * | 6/2003 | Deem et al. ..................... 606/1 |
| 6,656,194 B1 | 12/2003 | Gannoe et al. | 2003/0149467 A1 * | 8/2003 | Linder et al. ................ 623/1.11 |
| 6,669,722 B2 | 12/2003 | Chen et al. | 2003/0153927 A1 | 8/2003 | DiPoto et al. |
| 6,675,809 B2 | 1/2004 | Stack et al. | 2003/0191476 A1 | 10/2003 | Smit |
| 6,676,692 B2 | 1/2004 | Rabkin et al. | 2003/0199989 A1 | 10/2003 | Stack et al. |
| 6,695,875 B2 | 2/2004 | Stelter et al. | 2003/0199990 A1 | 10/2003 | Stack et al. |
| 6,699,263 B2 | 3/2004 | Cope | 2003/0199991 A1 | 10/2003 | Stack et al. |
| 6,699,278 B2 | 3/2004 | Fischell et al. | 2003/0208260 A1 | 11/2003 | Lau et al. |
| 6,706,061 B1 | 3/2004 | Fischell et al. | 2003/0216749 A1 | 11/2003 | Ishikawa et al. |
| 6,716,240 B2 | 4/2004 | Fischell et al. | 2003/0233140 A1 | 12/2003 | Hartley et al. |
| 6,736,840 B2 | 5/2004 | Fischell et al. | 2004/0019388 A1 | 1/2004 | Starkebaum |
| 6,740,121 B2 | 5/2004 | Geitz | 2004/0024386 A1 | 2/2004 | Deem et al. |
| 6,755,869 B2 | 6/2004 | Geitz | 2004/0037865 A1 | 2/2004 | Miller |
| 6,764,518 B2 | 7/2004 | Godin | 2004/0039452 A1 | 2/2004 | Bessler |
| 6,773,440 B2 | 8/2004 | Gannoe et al. | 2004/0044357 A1 | 3/2004 | Gannoe et al. |
| 6,776,791 B1 | 8/2004 | Stallings et al. | 2004/0082963 A1 | 4/2004 | Gannoe et al. |
| 6,802,868 B2 | 10/2004 | Silverman et al. | 2004/0092892 A1 | 5/2004 | Kagan et al. |
| 6,821,291 B2 | 11/2004 | Bolea et al. | 2004/0092974 A1 | 5/2004 | Gannoe et al. |
| 6,845,776 B2 | 1/2005 | Stack et al. | 2004/0093065 A1 | 5/2004 | Yachia et al. |
| 6,860,899 B1 | 3/2005 | Rivelli, Jr. | 2004/0098079 A1 | 5/2004 | Hartley et al. |
| 6,860,901 B1 | 3/2005 | Baker et al. | 2004/0107004 A1 | 6/2004 | Levine et al. |
| 6,936,065 B2 | 8/2005 | Khan et al. | 2004/0117004 A1 | 6/2004 | Osborne et al. |
| 6,960,233 B1 | 11/2005 | Berg et al. | 2004/0117031 A1 | 6/2004 | Stack et al. |
| 6,989,024 B2 * | 1/2006 | Hebert et al. ............... 623/1.11 | 2004/0122452 A1 | 6/2004 | Deem et al. |
| 7,011,654 B2 * | 3/2006 | Dubrul et al. ............... 604/508 | 2004/0122453 A1 | 6/2004 | Deem et al. |
| 7,011,671 B2 * | 3/2006 | Welch ........................ 606/194 | 2004/0122470 A1 | 6/2004 | Deem et al. |
| 7,011,673 B2 | 3/2006 | Fischell et al. | 2004/0133147 A1 | 7/2004 | Woo |
| 7,025,791 B2 | 4/2006 | Levine et al. | 2004/0136971 A1 | 7/2004 | Scharp et al. |
| 7,033,384 B2 | 4/2006 | Gannoe et al. | 2004/0138525 A1 | 7/2004 | Saadat et al. |
| 7,037,327 B2 | 5/2006 | Salmon et al. | 2004/0138529 A1 | 7/2004 | Wiltshire et al. |

| | | |
|---|---|---|
| 2004/0138760 A1 | 7/2004 | Schurr |
| 2004/0138761 A1 | 7/2004 | Stack et al. |
| 2004/0143342 A1 | 7/2004 | Stack et al. |
| 2004/0148034 A1 | 7/2004 | Kagan et al. |
| 2004/0153167 A1 | 8/2004 | Stack et al. |
| 2004/0158229 A1 | 8/2004 | Quinn |
| 2004/0158331 A1 | 8/2004 | Stack et al. |
| 2004/0172063 A1 | 9/2004 | Li et al. |
| 2004/0172088 A1 | 9/2004 | Knudson et al. |
| 2004/0172141 A1 | 9/2004 | Stack et al. |
| 2004/0172142 A1 | 9/2004 | Stack et al. |
| 2004/0172143 A1 | 9/2004 | Geitz |
| 2004/0181242 A1 | 9/2004 | Stack et al. |
| 2004/0193093 A1 | 9/2004 | Desmond, III |
| 2004/0210243 A1 | 10/2004 | Gannoe et al. |
| 2004/0220682 A1 | 11/2004 | Levine et al. |
| 2004/0236363 A1 | 11/2004 | Kieturakis et al. |
| 2004/0236401 A1 | 11/2004 | Shin et al. |
| 2004/0249362 A1 | 12/2004 | Levine et al. |
| 2005/0004681 A1 | 1/2005 | Stack et al. |
| 2005/0043601 A1 | 2/2005 | Kilcoyne et al. |
| 2005/0043817 A1 | 2/2005 | McKenna et al. |
| 2005/0049718 A1 | 3/2005 | Dann et al. |
| 2005/0055039 A1* | 3/2005 | Burnett et al. ............... 606/151 |
| 2005/0060017 A1 | 3/2005 | Fischell et al. |
| 2005/0075622 A1 | 4/2005 | Levine et al. |
| 2005/0080395 A1 | 4/2005 | Levine et al. |
| 2005/0080431 A1 | 4/2005 | Levine et al. |
| 2005/0080491 A1 | 4/2005 | Levine et al. |
| 2005/0085923 A1 | 4/2005 | Levine et al. |
| 2005/0090873 A1 | 4/2005 | Imran |
| 2005/0096750 A1 | 5/2005 | Kagan et al. |
| 2005/0125020 A1 | 6/2005 | Meade et al. |
| 2005/0125075 A1 | 6/2005 | Meade et al. |
| 2005/0149114 A1* | 7/2005 | Cartledge et al. ........... 606/213 |
| 2005/0171556 A1 | 8/2005 | Murphy |
| 2005/0192614 A1 | 9/2005 | Binmoeller |
| 2005/0216040 A1 | 9/2005 | Gertner et al. |
| 2005/0216042 A1 | 9/2005 | Gertner |
| 2005/0221072 A1 | 10/2005 | Dubrow et al. |
| 2005/0228415 A1 | 10/2005 | Gertner |
| 2005/0228504 A1 | 10/2005 | Demarais |
| 2005/0240279 A1 | 10/2005 | Kagan et al. |
| 2005/0256587 A1 | 11/2005 | Egan |
| 2005/0267499 A1 | 12/2005 | Stack et al. |
| 2005/0267533 A1 | 12/2005 | Gertner |
| 2005/0283107 A1 | 12/2005 | Kalanovic et al. |
| 2006/0009858 A1 | 1/2006 | Levine et al. |
| 2006/0064120 A1 | 3/2006 | Levine et al. |
| 2006/0106332 A1 | 5/2006 | Knudson et al. |
| 2006/0155312 A1* | 7/2006 | Levine et al. ................ 606/153 |
| 2006/0161139 A1 | 7/2006 | Levine et al. |
| 2006/0161172 A1 | 7/2006 | Levine et al. |
| 2006/0161187 A1 | 7/2006 | Levine et al. |
| 2006/0161265 A1 | 7/2006 | Levine et al. |
| 2006/0212042 A1 | 9/2006 | Lamport et al. |
| 2006/0265082 A1 | 11/2006 | Meade et al. |
| 2006/0287734 A1 | 12/2006 | Stack et al. |
| 2007/0005147 A1 | 1/2007 | Levine et al. |
| 2007/0010864 A1 | 1/2007 | Dann et al. |
| 2007/0027548 A1 | 2/2007 | Levine et al. |
| 2007/0032879 A1 | 2/2007 | Levine et al. |
| 2007/0049801 A1 | 3/2007 | Lamport et al. |
| 2007/0083271 A1* | 4/2007 | Levine et al. ............ 623/23.64 |
| 2007/0282453 A1 | 12/2007 | Weitzner et al. |
| 2007/0293885 A1 | 12/2007 | Binmoeller |
| 2008/0071383 A1 | 3/2008 | Levine et al. |
| 2008/0103604 A1 | 5/2008 | Levine et al. |
| 2008/0208239 A1 | 8/2008 | Annunziata |
| 2008/0208240 A1 | 8/2008 | Paz |
| 2008/0208357 A1 | 8/2008 | Melanson et al. |
| 2008/0221575 A1 | 9/2008 | Betts |
| 2008/0223476 A1 | 9/2008 | Stinson |
| 2008/0234834 A1 | 9/2008 | Meade et al. |
| 2008/0293885 A1 | 11/2008 | Morimoto et al. |
| 2009/0012553 A1 | 1/2009 | Swain et al. |
| 2009/0024077 A1 | 1/2009 | Zeiner et al. |
| 2009/0062717 A1 | 5/2009 | Laufer |
| 2009/0281563 A1 | 11/2009 | Newell et al. |

FOREIGN PATENT DOCUMENTS

| | | |
|---|---|---|
| EP | 0 480 667 B1 | 4/1992 |
| EP | 0278937 B1 | 10/1993 |
| EP | 0 506 918 B1 | 1/1996 |
| EP | 0754017 B1 | 1/1997 |
| EP | 0843538 B1 | 5/1998 |
| EP | 0 857 471 A2 | 8/1998 |
| EP | 0935977 A2 | 8/1999 |
| EP | 0935977 A3 | 8/1999 |
| EP | 1 481 649 A1 | 12/2004 |
| EP | 1 504 778 A2 | 2/2005 |
| EP | 1 504 778 A3 | 2/2005 |
| JP | 04212348 | 8/1992 |
| WO | WO 92/06734 | 4/1992 |
| WO | WO 95/05132 A | 2/1995 |
| WO | WO 97/03624 | 2/1997 |
| WO | WO 98/22045 A | 5/1998 |
| WO | WO 99/23953 A | 5/1999 |
| WO | WO 99/44536 A | 9/1999 |
| WO | WO 00/12027 | 3/2000 |
| WO | WO 00/28922 | 5/2000 |
| WO | WO 00/32137 | 6/2000 |
| WO | WO 00/42945 | 7/2000 |
| WO | WO 00/42949 | 7/2000 |
| WO | WO 01/12256 A1 | 2/2001 |
| WO | WO 01/35861 A1 | 5/2001 |
| WO | WO 01/45485 A2 | 6/2001 |
| WO | WO 02/081019 A1 | 10/2002 |
| WO | WO 02/096327 A2 | 12/2002 |
| WO | WO 03/017882 A2 | 3/2003 |
| WO | WO 03/086246 A1 | 10/2003 |
| WO | WO 03/086247 A1 | 10/2003 |
| WO | WO 03/086360 A1 | 10/2003 |
| WO | WO 03/094785 A1 | 11/2003 |
| WO | WO 2004/000169 A1 | 12/2003 |
| WO | WO 2004/004542 A2 | 1/2004 |
| WO | WO 2004/004542 A3 | 1/2004 |
| WO | WO 2004/014237 A1 | 2/2004 |
| WO | WO 2004/019765 A2 | 3/2004 |
| WO | WO 2004/019765 A3 | 3/2004 |
| WO | WO 2004/021894 A1 | 3/2004 |
| WO | WO 2004/037064 A2 | 5/2004 |
| WO | WO 2004/037064 A3 | 5/2004 |
| WO | WO 2004/049982 A2 | 6/2004 |
| WO | WO 2004/064680 A1 | 8/2004 |
| WO | WO 2004/064682 A1 | 8/2004 |
| WO | WO 2004/064685 A1 | 8/2004 |
| WO | WO 2004/069331 A2 | 8/2004 |
| WO | WO 2004/069332 A1 | 8/2004 |
| WO | WO 2004/073782 A1 | 9/2004 |
| WO | WO 2004/087014 A2 | 10/2004 |
| WO | WO 2004/087233 A2 | 10/2004 |
| WO | WO 2004/093639 A2 | 11/2004 |
| WO | WO 2004/093639 A3 | 11/2004 |
| WO | WO 2005/011533 A1 | 2/2005 |
| WO | WO 2005/060869 A1 | 7/2005 |
| WO | WO 2005/060882 A1 | 7/2005 |
| WO | WO 2005/082296 A1 | 9/2005 |
| WO | WO 2005/110280 A2 | 11/2005 |
| WO | WO 2005/110280 A3 | 11/2005 |
| WO | WO 2005/117716 A2 | 12/2005 |
| WO | WO 2005/118049 A1 | 12/2005 |
| WO | WO 2005/120363 A1 | 12/2005 |
| WO | WO 2006/016894 A1 | 2/2006 |
| WO | WO 2006/034062 A1 | 3/2006 |

| WO | WO 2006/078781 | A1 | 7/2006 |
| WO | WO 2006/078927 | A1 | 7/2006 |
| WO | WO 2006/088578 | A1 | 8/2006 |
| WO | WO 2006/102012 | A1 | 9/2006 |
| WO | WO 2006/133311 | A2 | 12/2006 |

OTHER PUBLICATIONS

Binkert, C. A., et al., "Benign and Malignant Stenoses of the Stomach and Duodenum: Treatment with Self-Expanding Metallic Endoprotheses[1]," *Radiology*, 199(2): 335-338 (May 1996).

CHOOSTENT™, Covered Esophageal Stent, Instructions, Retrieved from the Internet (http://mitech.co.kr/uploads/images/282/use guide esophachoo_english.pdf on Jul. 26, 2005.

Cwikiel, W., et al., "Self-Expanding Stent in the Treatment of Benign Esophageal Strictures: Experimental Study in Pigs and Presentation of Clinical Cases[1]," *Radiology* 187(3): 667-671 (Jun. 1993).

Dolan, K. et al., "Treating Diabetes in the Morbidly Obese by Laparoscopic Gastric Banding," *Obesity Surgery*, 13:439-443 (2003).

Dormann, A.J. et al., "Self-Expanding Metallic Stents for Continuous Dilation of Benign Stenosis in Gastrointestinal Tract-First Results of Long-Term Follow-Up inIinterim Stent Application in Pyloric and Colonic Obstructions," *Z. Gastroenteral.*, 39:957-960 (2001).

Feretis, C., et al., "Palliation of Malignant Gastric Outlet Obstruction with Self-Expanding Metal Stents," *Endoscopy*, 28:225-228 (Feb. 1996).

Hwang, J.C., et al., "Covered Retrievable Tracheobronichial Hinged Stent: An Experimental Study in Dogs," *J. Vasc. Interv. Radiol.*, 12(12):1429-1436 (Dec. 2001).

Irie, T., et al., "Relocatable Gianturco Expandable Metallic Stents[1]," *Radiology*, 178:575-578 (1991).

Lee, B.H., et al., "New Self-Expandable Spiral Metallic Stent: Preliminary clinical Evaluation in Malignant Biliary Obstruction," *J. Vasc Interv Radiol.*, 6(4):635-640 (Jul.-Aug. 1995).

Lee, S.H., "The Role of Oesophageal Stenting in the Non-Surgical Management of Oesophageal Strictures," *British J. Radiology*, 74:891-900 (Oct. 2001).

Park, B.P. et al., "Malignant Obstruction of Gastric Outlet and Duodenum: Palliation with Flexible Covered Metallic Stents[1]," *Radiology*, 219(3):679-683 (Jun. 2001).

Parodi, J.C., M.D., "Endovascular Repair of Abdominal Aortic Aneurysms," *Advances in Vascular Surgery*, 1:85-106 (1993).

Pories, W.J., "Why Does the Gastric Bypass Control Type 2 Diabetes Mellitus?" *Obesity Surgery*, 2:303-313 (1992).

Pories, W.J., et al., "Etiology of Type II Diabetes Mellitus: Role of the Foregut," *World J. Surg.*, 25(4):527-531 (Apr. 2001).

Rubino, F. and J. Marescaux, "Effect of Duodenal-Jejunal Exclusion in a Non-obese Animal Model of Type 2 Diabetes, A New Perspective for an Old Disease," *Annals of Surgery* 239(1):1-11 (Jan. 2004).

Rubino, F., et al., "Potential of Surgery for Curing Type 2 Diabetes Mellitus," *Annals of Surgery*, 236(5):554-559 (Nov. 2002).

Sandha, G. S. and Marcon, N.E., "Expandable Metal Stents For Benign Esophageal Obstruction," *Gastrointentinal Endoscopy Clinics of North America* 9(3):437-446 (Jul. 1999).

Shim, C.S., et al., "Fixation of a Modified Covered Esophageal Stent: Its Clinical Usefulness for Preventing Stent Migration," *Endoscopy*, 33(10):843-848 (Oct. 2001).

Song, H.Y., et al., "Benign and Malignant Esophageal Strictures: Treatment with a Polyurethane-Covered Retrievable Expandable Metallic Stent[1]," *Radiology*, 203(3):747-752 (Jun. 1997).

Song, H.Y., et al., "Covered Retrievable Expandable Nitinol Stents in Patients with Benign Esophageal Strictures: Initial Experience[1]," *Radiology*, 217:551-557 (Nov. 2000).

Song, H.Y., et al., "Tracheobronchial Strictures: Treatment with a Polyurethane-Covered Retrievable Expandable Nitinol Stent—Initial Experience," *Radiology*, 213:905-912 (Dec. 1999).

Yates III, M. R., et al., "Palliation of Malignant Gastric and Small Intestinal Strictures With Self-Expandable Metal Stents," *Endoscopy*, 30:266-272 (Mar. 1998).

Yoon, C.J., et al., "Removal of Retrievable Esophageal and Gastrointestinal Stents: Experience in 113 Patients," *American J. of Roentgenology*, 183:1437-1444 (Nov. 2004).

Notice of Allowance of U.S. Appl. No. 11/302,977, mailed Dec. 29, 2009.

U.S. Office Action in U.S. Appl. No. 11/302,977, mailed on Jun. 1, 2009.

U.S. Office Action in U.S. Appl. No. 11/541,616, mailed on Mar. 17, 2009.

* cited by examiner

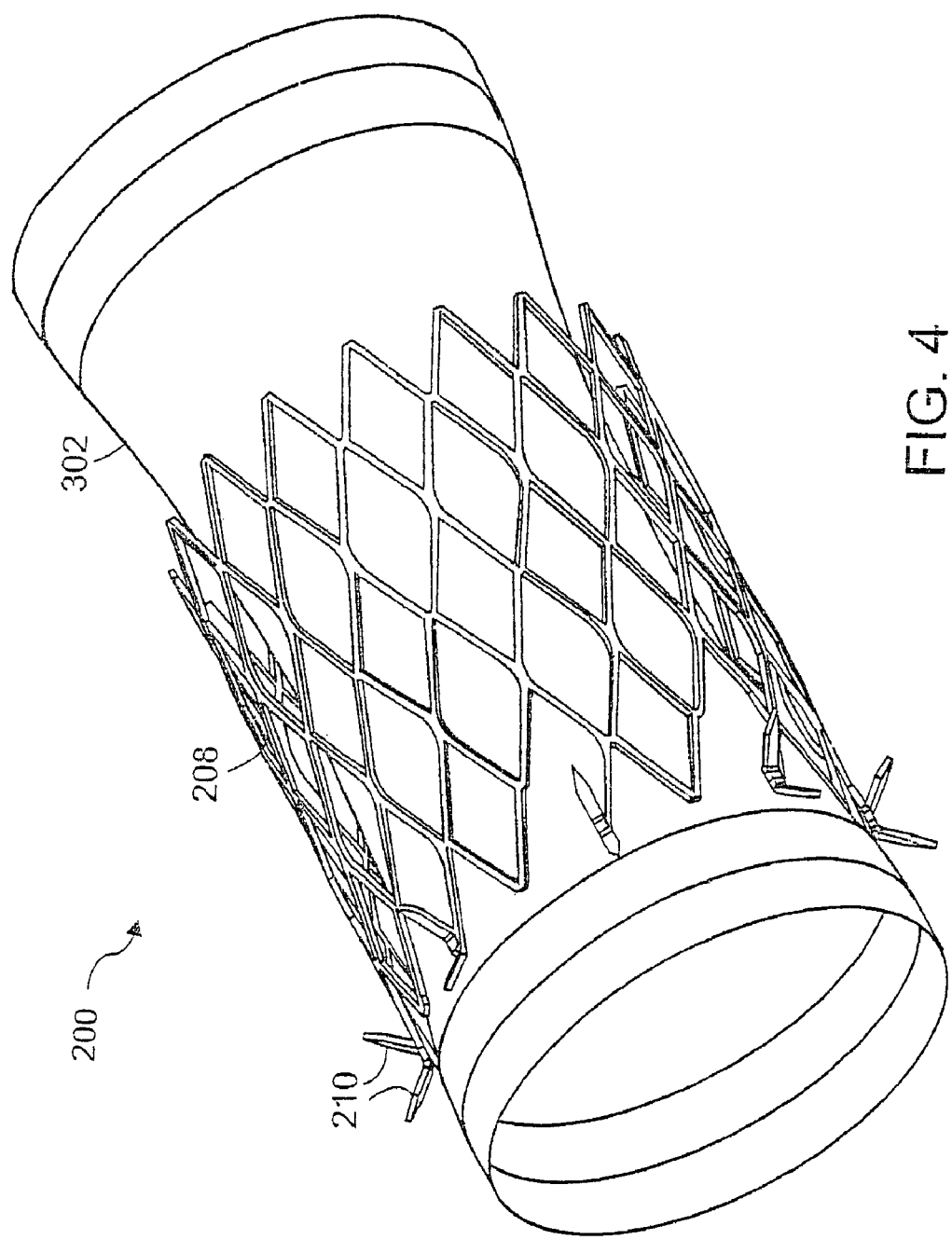

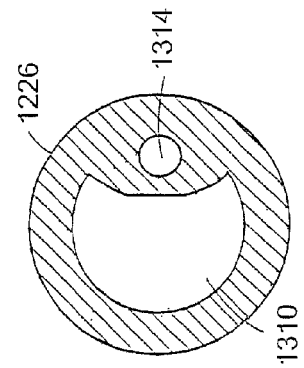
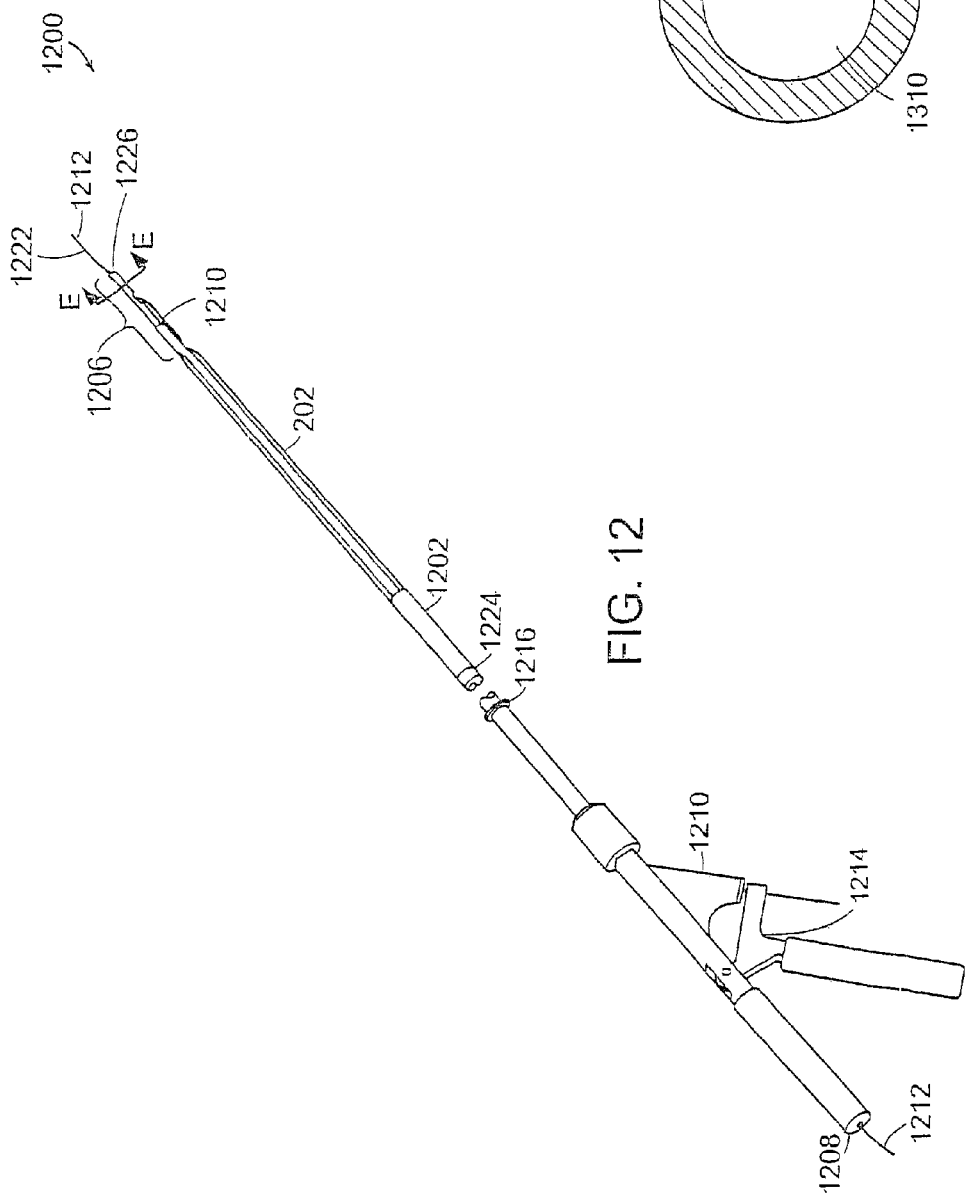

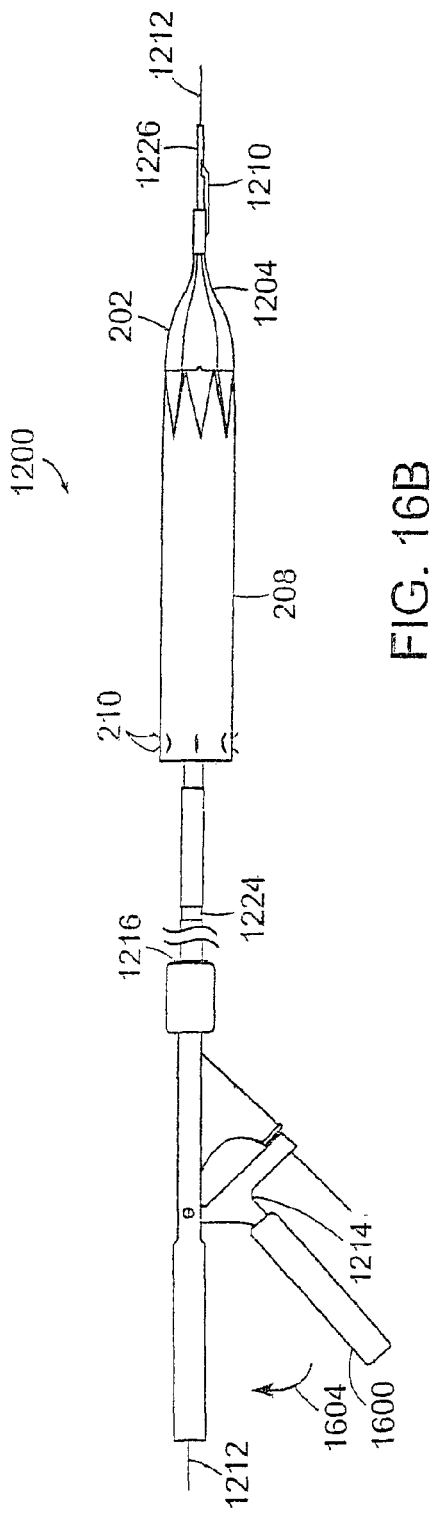
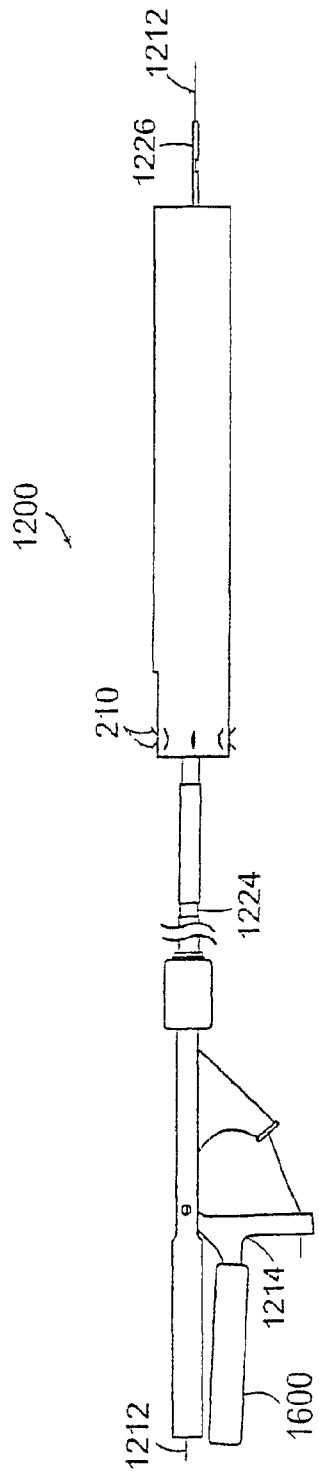
FIG. 16B
FIG. 16C

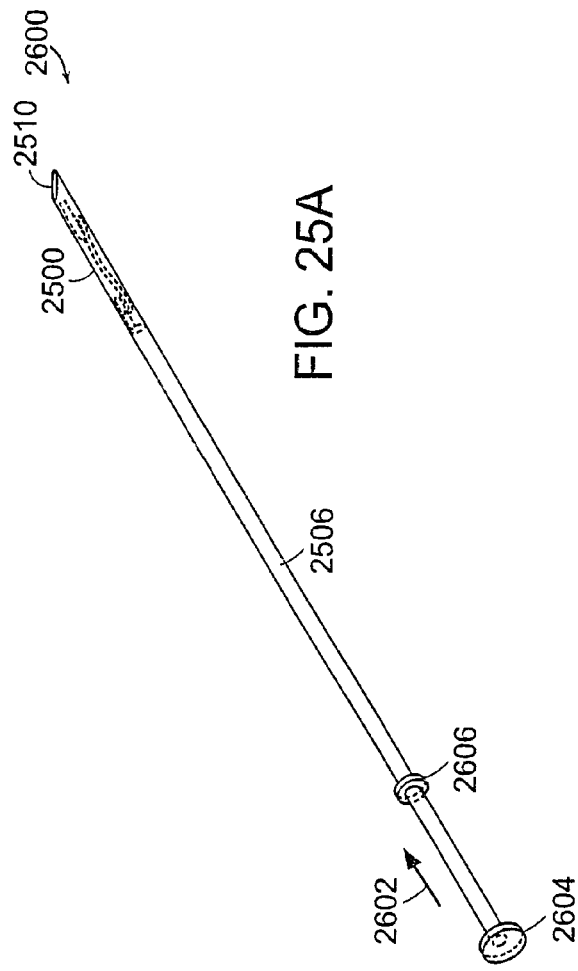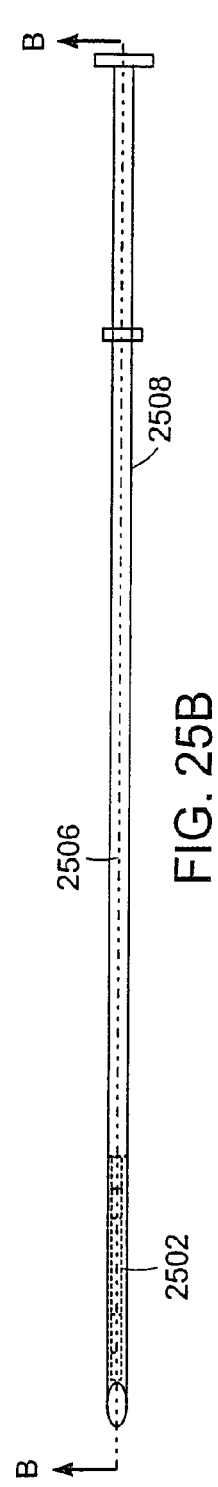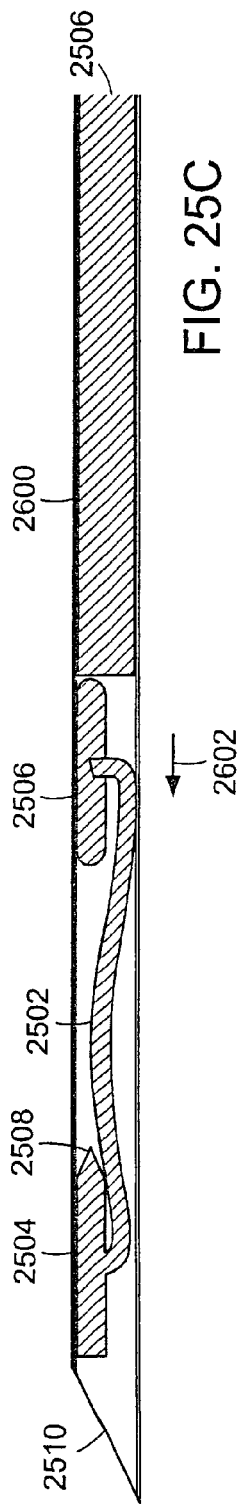

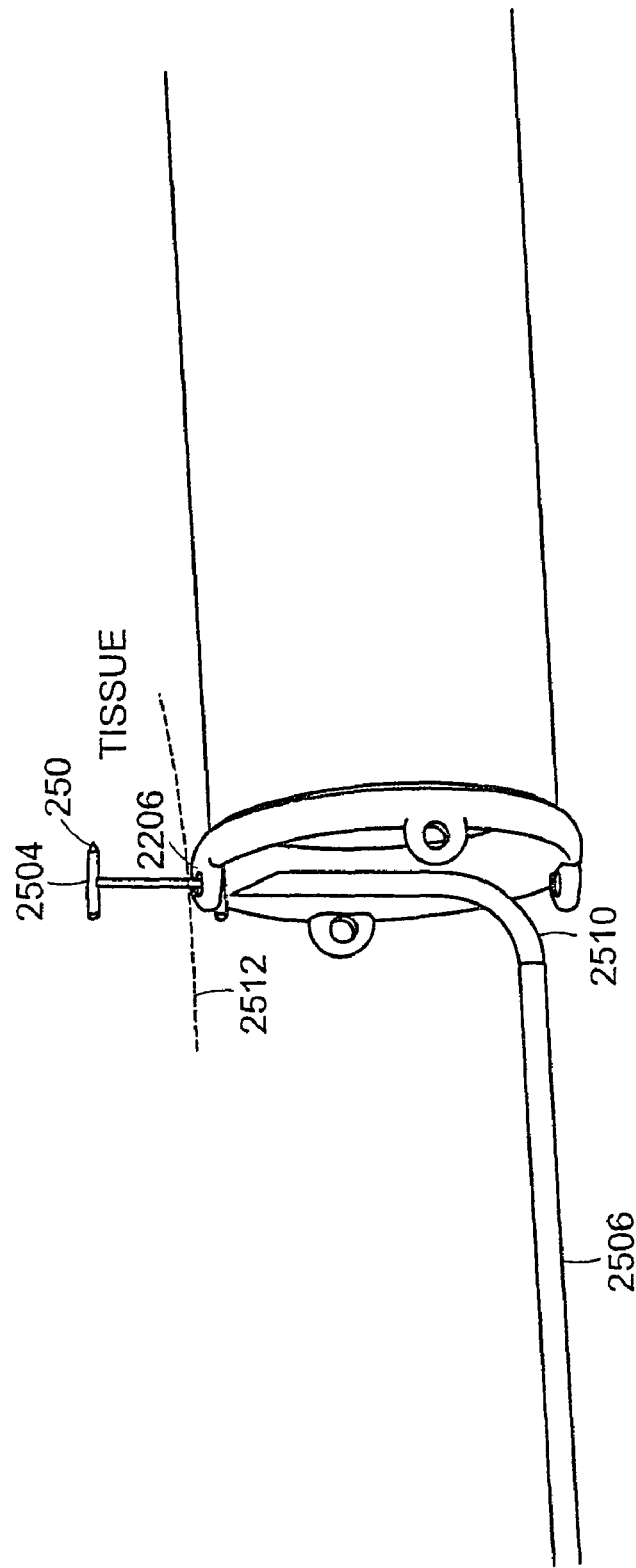

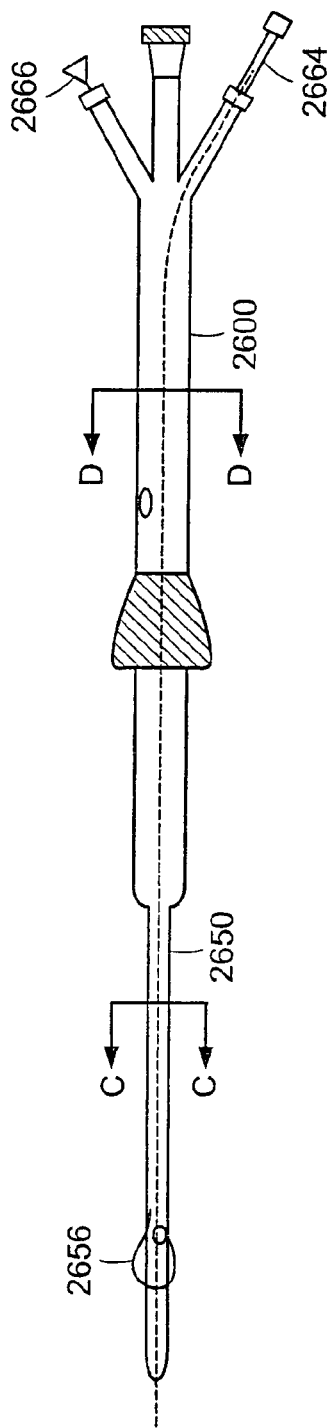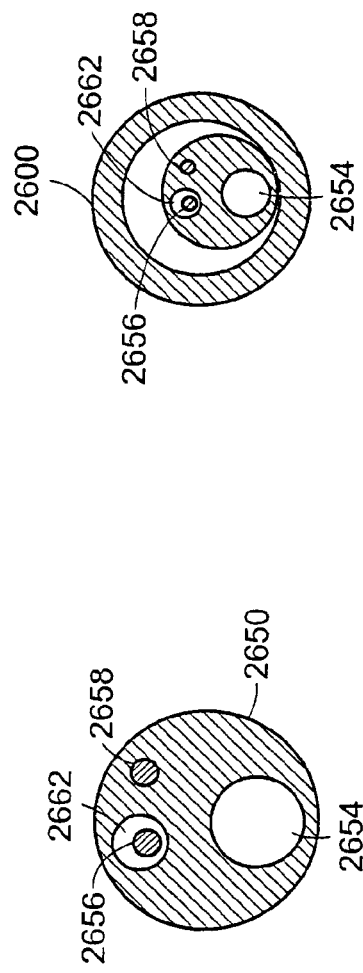
FIG. 26A
FIG. 26B
FIG. 26C

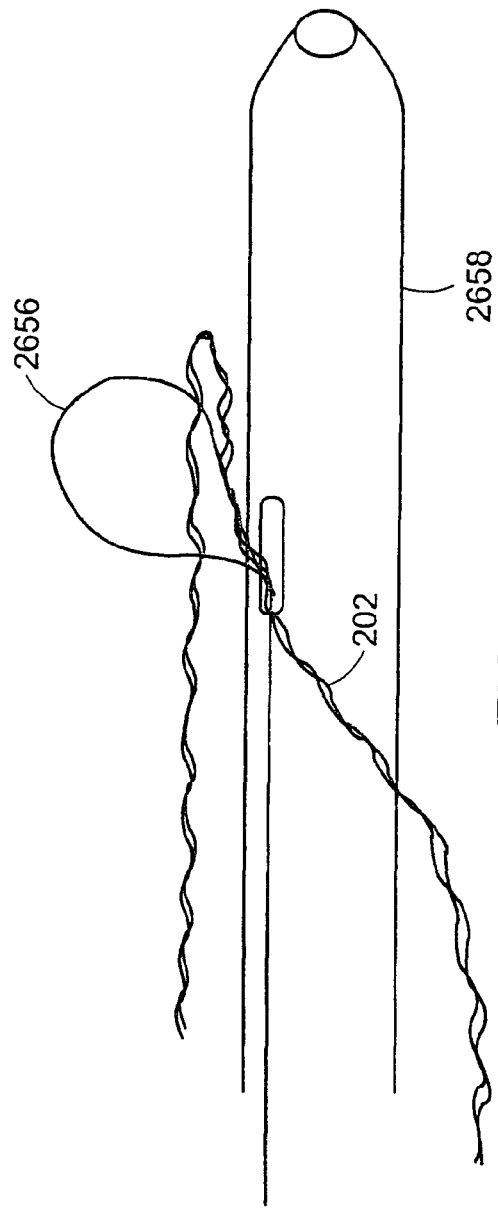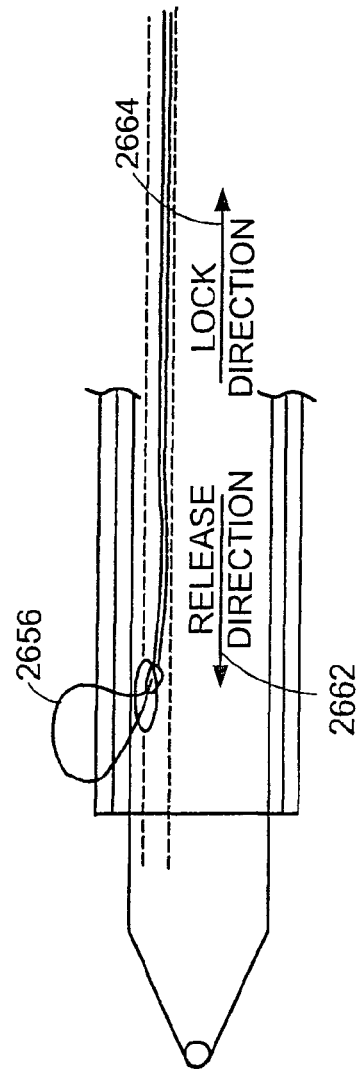

BARIATRIC SLEEVE DELIVERY DEVICES

RELATED APPLICATIONS

This application is a continuation-in-part of U.S. application Ser. No. 10/999,846, now U.S. Pat. No. 7,329,285, filed Nov. 30, 2004, which is a divisional of U.S. application Ser. No. 10/339,786, now U.S. Pat. No. 7,025,791, filed Jan. 9, 2003, which claims the benefit of U.S. Provisional Application No. 60/430,321, filed on Dec. 2, 2002. The entire teachings of the above applications are incorporated herein by reference.

BACKGROUND OF THE INVENTION

According to the Center for Disease Control (CDC), over sixty percent of the United States population is overweight, and almost twenty percent are obese. This translates into 38.8 million adults in the United States with a Body Mass Index (BMI) of 30 or above. The BMI is defined as a person's weight (in kilograms) divided by height (in meters), squared. To be considered clinically, morbidly obese, one must meet one of three criteria: BMI over 35, 100 lbs. overweight or 100% above ideal body weight. There is also a category for the super-obese for those weighing over 350 lbs.

Obesity is an overwhelming health problem. Because of the enormous strain associated with carrying this excess weight, organs are affected, as are the nervous and circulatory systems. In 2000, the National Institute of Diabetes, Digestive and Kidney Diseases (NIDDK) estimated that there were 280,000 deaths directly related to obesity. The NIDDK further estimated that the direct cost of healthcare in the US associated with obesity is $51 billion. In addition, Americans spend $33 billion per year on weight loss products. In spite of this economic cost and consumer commitment, the prevalence of obesity continues to rise at alarming rates. From 1991 to 2000, obesity in the US grew by 61%. Not exclusively a US problem, worldwide obesity ranges are also increasing dramatically.

One of the principle costs to the healthcare system stems from the co-morbidities associated with obesity. Type-2 diabetes has climbed to 7.3% of the population. Of those persons with Type-2 diabetes, almost half are clinically obese, and two thirds are approaching obese. Other co-morbidities include hypertension, coronary artery disease, hypercholesteremia, sleep apnea and pulmonary hypertension.

Although the physiology and psychology of obesity are complex, the medical consensus is that the cause is quite simple—an over intake of calories combined with a reduction in energy expenditures seen in modern society. While the treatment seems quite intuitive, the institution of a cure is a complex issue that has so far vexed the best efforts of medical science. Dieting is not an adequate long-term solution for most people. Once an individual has slipped past the BMI of 30, significant changes in lifestyle are the only solution.

There have been many attempts in the past to surgically modify patients' anatomies to attack the consumption problem by reducing the desire to eat. Stomach saplings, or gastroplasties, to reduce the volumetric size of the stomach, therein achieving faster satiety, were performed in the 1980's and early 1990's. Although able to achieve early weight loss, sustained reduction was not obtained. The reasons are not all known, but are believed related to several factors. One of which is that the stomach stretches over time increasing volume while psychological drivers motivate patients to find creative approaches to literally eat around the smaller pouch.

There are currently two surgical procedures that successfully produce long-term weight loss; the Roux-en-Y gastric bypass and the biliopancreatic diversion with duodenal switch (BPD). Both procedures reduce the size of the stomach plus shorten the effective-length of intestine available for nutrient absorption. Reduction of the stomach size reduces stomach capacity and the ability of the patient to take in food. Bypassing the duodenum makes it more difficult to digest fats, high sugar and carbohydrate rich foods. One objective of the surgery is to provide feedback to the patient by producing a dumping syndrome if they do eat these food products. Dumping occurs when carbohydrates directly enter the jejunum without being first conditioned in the duodenum. The result is that a large quantity of fluid is discharged into the food from the intestinal lining. The total effect makes the patient feel light-headed and results in severe diarrhea. For reasons that have not been determined the procedure also has an immediate therapeutic effect on diabetes.

Although the physiology seems simple, the exact mechanism of action in these procedures is not understood. Current theory is that negative feedback is provided from both regurgitation into the esophagus and dumping when large volumes of the wrong foods are eaten. Eventually, patients learn that to avoid both these issues they must be compliant with the dietary restrictions imposed by their modified anatomy. In the BPD procedure, large lengths of jejunum are bypassed resulting in malabsorption and therefore, reduced caloric uptake. In fact, the stomach is not reduced in size as much in the BPD procedure so that the patient is able to consume sufficient quantities of food to compensate for the reduced absorption. This procedure is reserved for the most morbidly obese as there are several serious side effects of prolonged malabsorption.

Unfortunately, these procedures carry a heavy toll. The morbidity rate for surgical procedures is alarmingly high with 11% requiring surgical intervention for correction. Early small bowel obstruction occurs at a rate of between 2-6% in these surgeries and mortality rates are reported to be approximately 0.5-1.5%. While surgery seems to be an effective answer, the current invasive procedures are not acceptable with these complication rates. Laparoscopic techniques applied to these surgeries provide fewer surgical complications but continue to expose these very ill patients to high operative risk in addition to requiring an enormous level of skill by the surgeon. Devices to reduce absorption in the small intestines have been proposed (See U.S. Pat. No. 5,820,584 (Crabb), U.S. Pat. No. 5,306,300 (Berry) and U.S. Pat. No. 4,315,509 (Smit)). However, these devices have not been successfully implemented.

SUMMARY OF THE INVENTION

A gastrointestinal implant device includes a flexible sleeve and a sleeve anchor, which may be a stent including a network of struts, coupled to a proximal portion of the sleeve. The flexible sleeve is open at both ends, and adapted to extend into the duodenum to limit absorption of nutrients in the duodenum. The sleeve anchor is adapted to be retained within the digestive system. For example, the device may be anchored distal to the pylorus, leaving the pylorus to function normally, or a stent may be retained within the pyloric orifice to hold the pylorus open.

A delivery system for placing a gastrointestinal implant device in a body includes an outer sheath for storing a proximal portion of the implant device, an inner sheath within the outer sheath, and a ball coupled to the distal end of the inner sheath to guide the delivery system through the alimentary canal. The ball is generally dimensioned to permit it to be pulled-back through a central lumen of the implant device. The inner sheath defines a lumen and extends distally beyond the outer sheath. The delivery system also includes a moveable element that is moveable within the lumen of the inner sheath. The moveable element is adapted to secure the distal end of the sleeve to the inner sheath. A sleeve release mechanism is coupled to the moveable element for releasing the distal end of the sleeve and an anchor release mechanism is also provided to release the sleeve anchor from the outer sheath. The inner sheath of the delivery system may define a second lumen for passing the outer sheath over a guidewire.

In operation, the anchor release mechanism pulls the outer sheath toward the proximal end of the delivery system to remove the outer sheath from the sleeve anchor. Similarly, the sleeve release mechanism pulls the moveable element toward the proximal end of the delivery system to release the distal end of the sleeve after the sleeve anchor has been released. The moveable element can be a sleeve retention wire, exiting the lumen of the inner sheath and piercing the distal end of the sleeve. Alternatively, the moveable element can be a snare wire capturing the distal end of the sleeve.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 4 is a perspective view of the gastrointestinal implant device with the second outer layer of the sleeve removed;

FIG. 12 is a perspective view of a catheter system for delivery of the gastrointestinal implant device;

FIG. 13 is a cross-sectional view of the inner shaft taken along line E-E of FIG. 12;

FIG. 16B is a plan view of the catheter system illustrating the gastrointestinal implant device after release of the stent from the outer sheath;

FIG. 16C is a plan view of the catheter system illustrating the expanded gastrointestinal implant device after the sleeve retention wire has been released;

FIG. 25A is a perspective view of a delivery system for delivering the anchor after the gastrointestinal implant device has been placed in the stomach;

FIG. 25B is a plan view of the delivery system shown in FIG. 25A;

FIG. 25C is a cross-sectional view of the distal end of the catheter as taken along line B-B of FIG. 25A;

FIG. 25E is a perspective view illustrating the barb engaging the tissue after delivery;

FIG. 26A is a plan view of the delivery system including a snare wire for holding the distal end of the sleeve in position;

FIG. 26B is a cross-sectional view taken along line CC of FIG. 26A through the inner sheath;

FIG. 26C is a cross-sectional view taken along line DD of FIG. 26A through the outer sheath showing the inner sheath within the outer sheath;

FIG. 26D is a cross-sectional view through the distal portion of the catheter showing the snare capturing the distal end of the sleeve;

FIG. 26E is a sectional view through the distal portion of the catheter showing the snare locking mechanism.

DETAILED DESCRIPTION OF THE INVENTION

A description of preferred embodiments of the invention follows.

Figure 1:
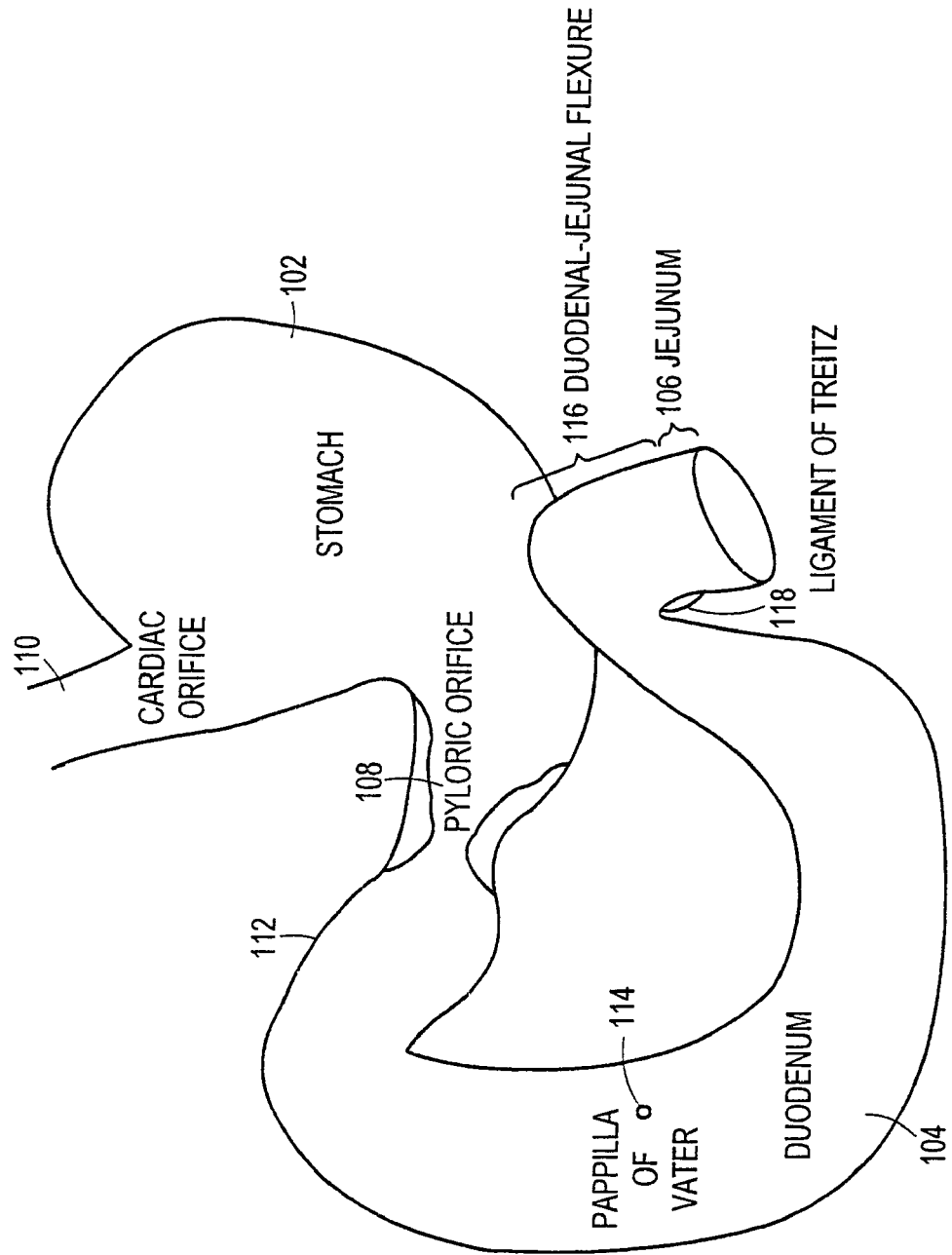
FIG. 1 is a sectional view of a portion of the digestive tract in a body.

FIG. 1 is a sectional view of a portion of the digestive tract in a body. Food to be digested enters the stomach 102 through the cardiac orifice 110 from the esophagus. Chyme, a semi-fluid, homogeneous creamy or gruel-like material produced by gastric digestion in the stomach exits the stomach through the pyloric orifice (pylorus) 108 and enters the small intestine 112. The pylorus 108 is a distal aperture of the stomach 102 surrounded by a strong band of circular muscle. The small intestine, about nine feet in length, is a convoluted tube, extending from the pylorus to the ileo-caecal valve where it terminates in the large intestine. The small intestine has three sections, the duodenum 104, jejunum 106 and the ileum (not shown). The first eight to ten inch section of the small intestine, the duodenum, is the shortest, widest and most fixed part of the small intestine.

The duodenum has four sections: superior, descending, transverse and ascending which typically form a U-shape. The superior section is about two inches long and ends at the neck of the gall bladder. The descending section is about three to four inches long and includes a nipple shaped structure (papilla of vater) 114 through which pancreatic juice from the pancreas and bile produced by the liver and stored by the gall bladder enter the duodenum from the pancreatic duct. The pancreatic juice contains enzymes essential to protein digestion and bile dissolves the products of fat digestion. The ascending section is about two inches long and forms the duodenal-jejunal flexure 116 where it joins the jejunum 106, the next section of the small intestine. The duodenal-jejunal flexure 116 is fixed to the ligament of Treitz 118 (musculus supensionus duodeni). The juices secreted in the duodenum break the partially digested food down into particles small enough to be absorbed by the body. The digestive system is described in Gray's Anatomy ("Anatomy of the Human Body", by Henry Gray) and "Human Physiology", Vander, $3^{rd}$ ed, McGraw Hill, 1980, the contents of which are incorporated herein by reference in their entirety.

Figure 2:
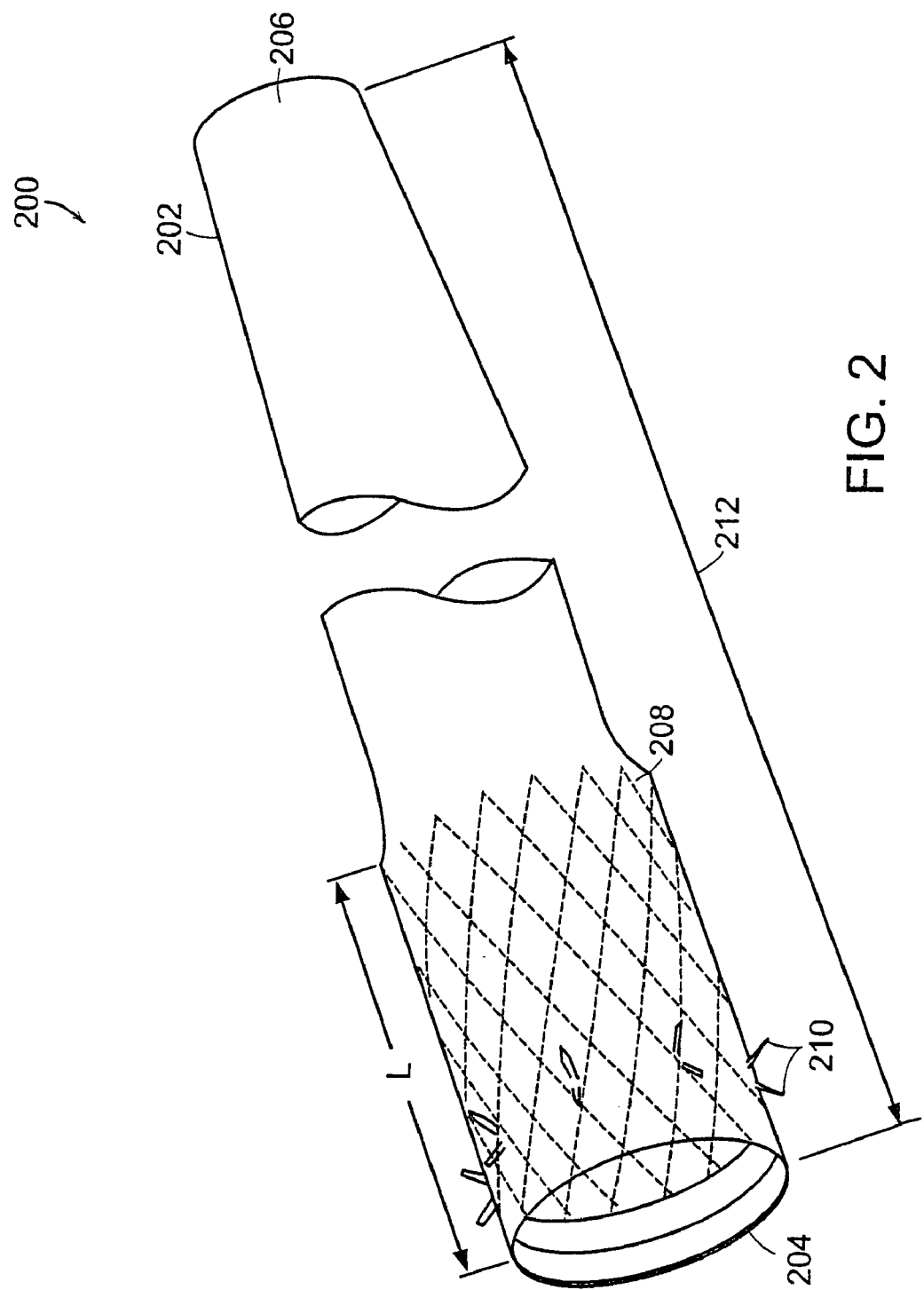
FIG. 2 is a perspective view of a gastrointestinal implant device according to the principles of the present invention.

FIG. 2 is a perspective view of a gastrointestinal implant device 200 according to the principles of the present invention. The gastrointestinal implant device 200 includes an elongated open-ended flexible sleeve or tube 202 having a first proximal opening 204 and a second distal opening 206. Within the sleeve 202 is a passageway that extends from the first proximal opening 204 to the second distal opening 206 for transporting the chyme exiting the stomach 102 (FIG. 1). The surface of the passageway (the interior surface of the implant device 200) is smooth to enable the chyme to easily pass through. The exterior surface of the implant device 200 is smooth to prevent tissue in-growth and to be non-irritating to the bowel.

Within the implant device 200 at the proximal end including the first proximal opening 204 is a collapsible self-expanding stent 208. The stent 208 includes a plurality of opposed barbs 210 for anchoring the implant device 200 to the muscular pylorus in the stomach 102. The diameter of the stent 208 is dependent on the diameter of the pyloric orifice 108 (FIG. 1) about 0.8" to 1.1" based on human anatomy variations. In one embodiment, the length l of the stent 208 is selected to extend through the pylorus 108 and keep the pylorus 108 permanently open to induce "dumping syndrome." In an alternate embodiment, a stent with a shorter length l allows the pylorus 108 to open and close normally.

The sleeve material is thin and conformable so that it collapses in the intestine to a small volume to minimize bowel irritability. It has a low coefficient of friction (<0.20) so that chyme slides easily through it and the bowel slides easily around it. It is of low permeability to fluids so that the chyme does not touch the bowel wall and the digestive enzymes do not significantly breakdown the chyme. It is biologically inert and non-irritating to the tissues. One such material is expanded polytetrafluoroethylene (ePTFE), a fluoropolymer, with a wall thickness of about 0.006" and an internodal distance of 20 microns. This material is hydrophobic but is slightly porous. However, these very small pores may plug over time. The porosity may be reduced by coating the material on the inside, outside or in the pores with dilute solutions of silicone or polyurethane. Another material is polyethylene with a wall thickness of less than 0.001". Rubber-like materials typically have friction coefficients of 1-4, significantly stickier than these materials. However, in alternate embodiments other materials having similar characteristics can be used.

The sleeve 202 includes two layers of material at least at the proximal end. A first outer layer covers the exterior of the stent. The second inner layer covers the interior surface of the stent 208. The barbs 210 protrude from the exterior surface of the stent 208 through the first outer layer of the sleeve 208. The holes in the first outer layer through which the barbs 210 protrude are filled with an impervious material such as silicone or urethane to limit mixing of digestive juices with the chyme flowing through the passageway. The diameter of the sleeve 208 is selected such that the first outer layer of the sleeve 208 fits over the stent 208.

The sleeve length 212 ranges from about one foot to about five feet. The typical length of the sleeve 208 is about 1.5 feet from the anchor (barbs 210) in the pyloric region of the stomach to below the ligament of Treitz 118 (FIG. 1). The length 212 of the sleeve 202 is selected to bypass the duodenum 104 (FIG. 1) and a portion of the jejunum. The length is increased to further decrease absorption by bypassing a longer section of the jejunum 106 (FIG. 1). The length 212 of the sleeve 202 is variable and dependent on the patient's Body Mass Index (BMI). The procedure is a less invasive alternative to surgery for the treatment of obesity and morbid obesity and also provides a new treatment approach for type 2 diabetes.

The covered stent 208 can be collapsed into a sheath having a diameter less than ¼ inch to enable endoscopic delivery. Covering the exterior surface of the stent 208 with the first outer layer of the sleeve 202 permits endoscopic removal of the implant device 200 by preventing tissue in-growth on the exterior surface of the stent 208.

Markings can be added to the exterior surface of the sleeve 202 to detect the position and orientation of the sleeve on a fluoroscopic image and whether the sleeve is twisted. For example, a stripe can be painted down the length of the device 200 using tantalum impregnated ink, or tantalum bands can be bonded to the exterior surface of the device. If the sleeve 202 is twisted, the sleeve 202 can be untwisted by inserting a balloon into the proximal end of the device thereby sealing it, and then injecting water into the sleeve at low pressure.

Figure 3A:
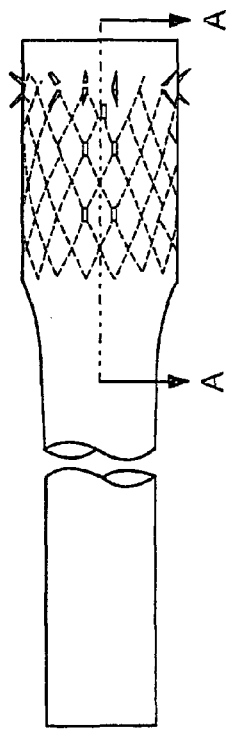
FIG. 3A is a plan view of the proximal portion of the gastrointestinal implant device shown in FIG. 2.
Figure 3B:
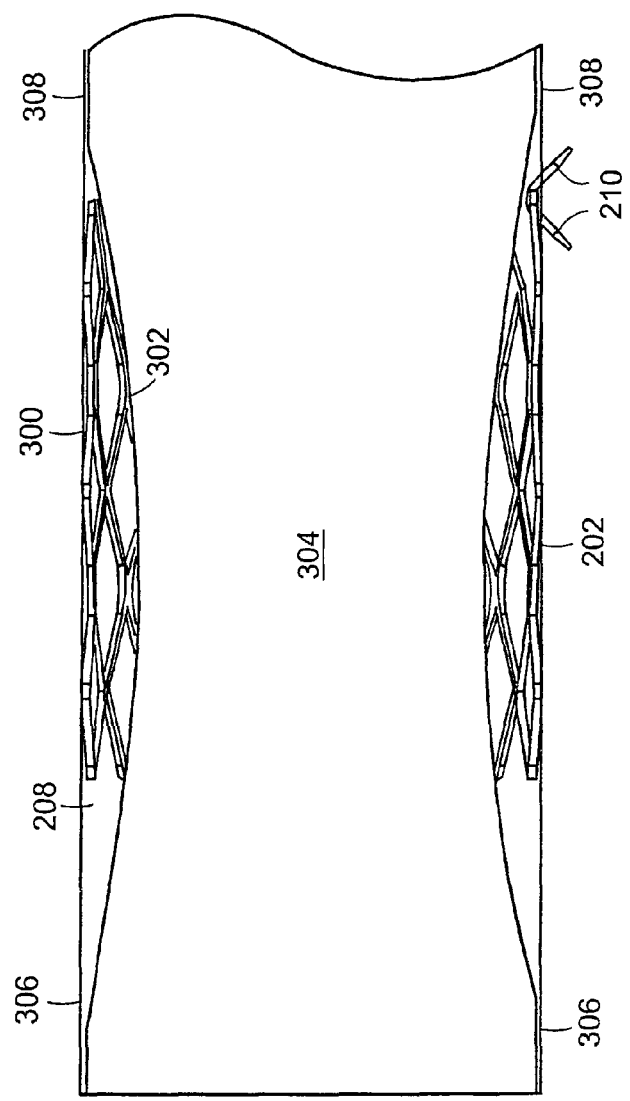
FIG. 3B is a cross-sectional view as taken along line A-A of FIG. 3A showing the stent and first inner layer and second outer layer of the sleeve shown in FIG. 2.

FIG. 3A is a plan view of the proximal portion of the gastrointestinal implant device shown in FIG. 2. FIG. 3B is a cross-sectional view as taken along line AA of FIG. 3A showing the stent 208 and the first outer layer 300 and the second inner layer 302 of the sleeve 202 shown in FIG. 2. As described in conjunction with FIG. 2, the sleeve 202 includes a first outer layer 300 and a second inner layer 302. The first outer layer 300 is bonded to the second inner layer 300 at positions 306 below the distal end of the stent 208 and at positions 308, above the proximal end of the stent 208. A passageway 304 inside the second inner layer 302 of the sleeve 202 allows passage of chyme through the sleeve 202. The stent 208 is sandwiched between the first outer layer 300 and the second inner layer 302 at the proximal end of the sleeve 202 and is free to move at the distal end within the first outer layer 300 and the second inner layer 302 of the sleeve 202. The covered exterior surface of the stent 208 prevents tissue growth to allow removal of the implant device 200. The covered interior surface of the stent 208 provides a smooth passageway for chyme to bypass the duodenum 104.

FIG. 4 is a perspective view of the gastrointestinal implant device 200 with the first outer layer 300 of the sleeve 202 removed. The interconnecting struts which form the mesh (a network of struts) with diamond spaced openings are sufficiently flexible to allow the stent to be collapsed inside a delivery catheter and have sufficient elasticity to hold the pylorus open once the catheter is withdrawn. The force needed to hold the pylorus open is about 1-2 lbs. of radial force outward when the stent is compressed from its full diameter by 25%.

Figure 5A:
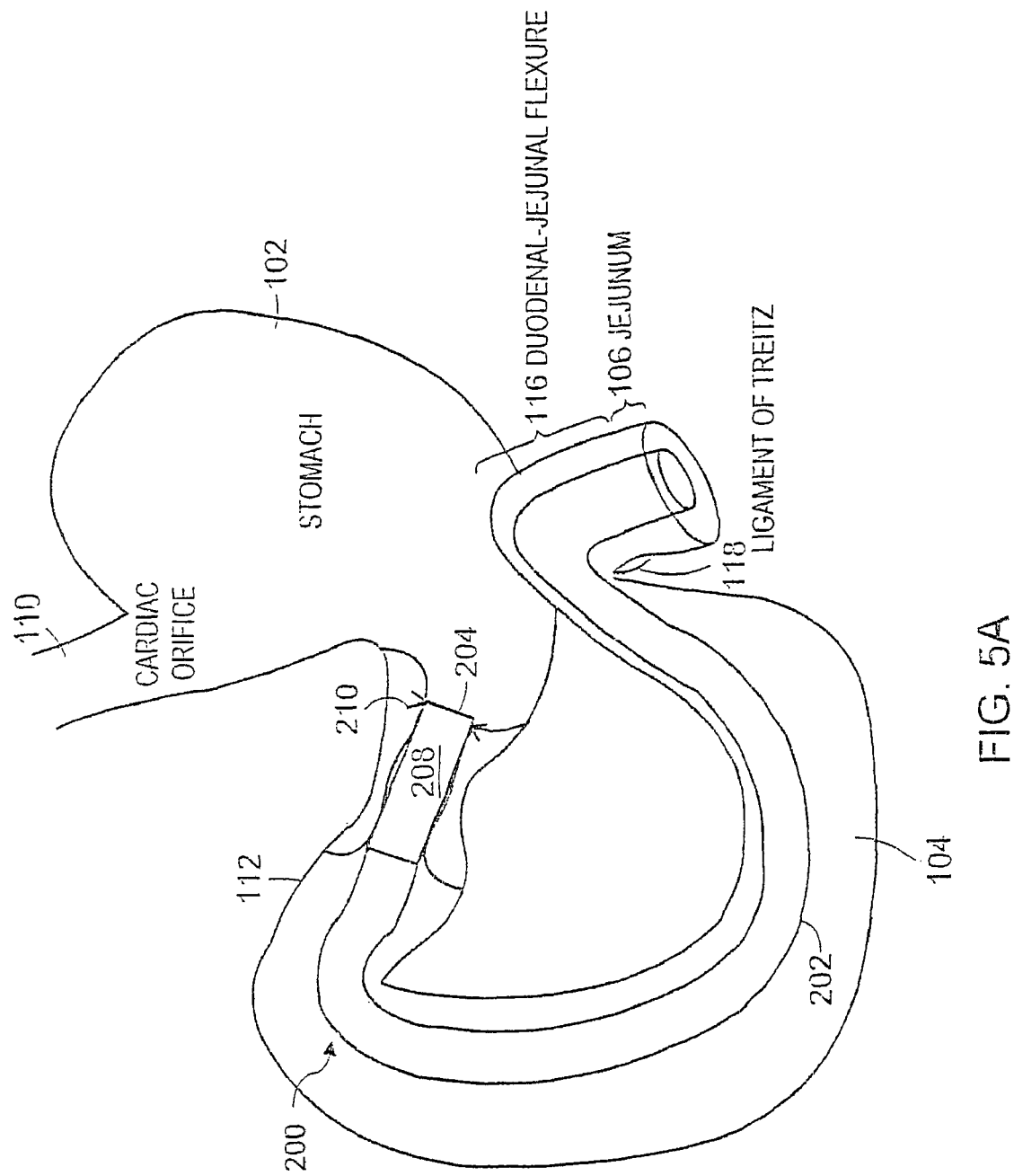
FIG. 5A is a sectional view of a body showing one embodiment of the gastrointestinal implant device implanted in the digestive system.
Figure 5B:
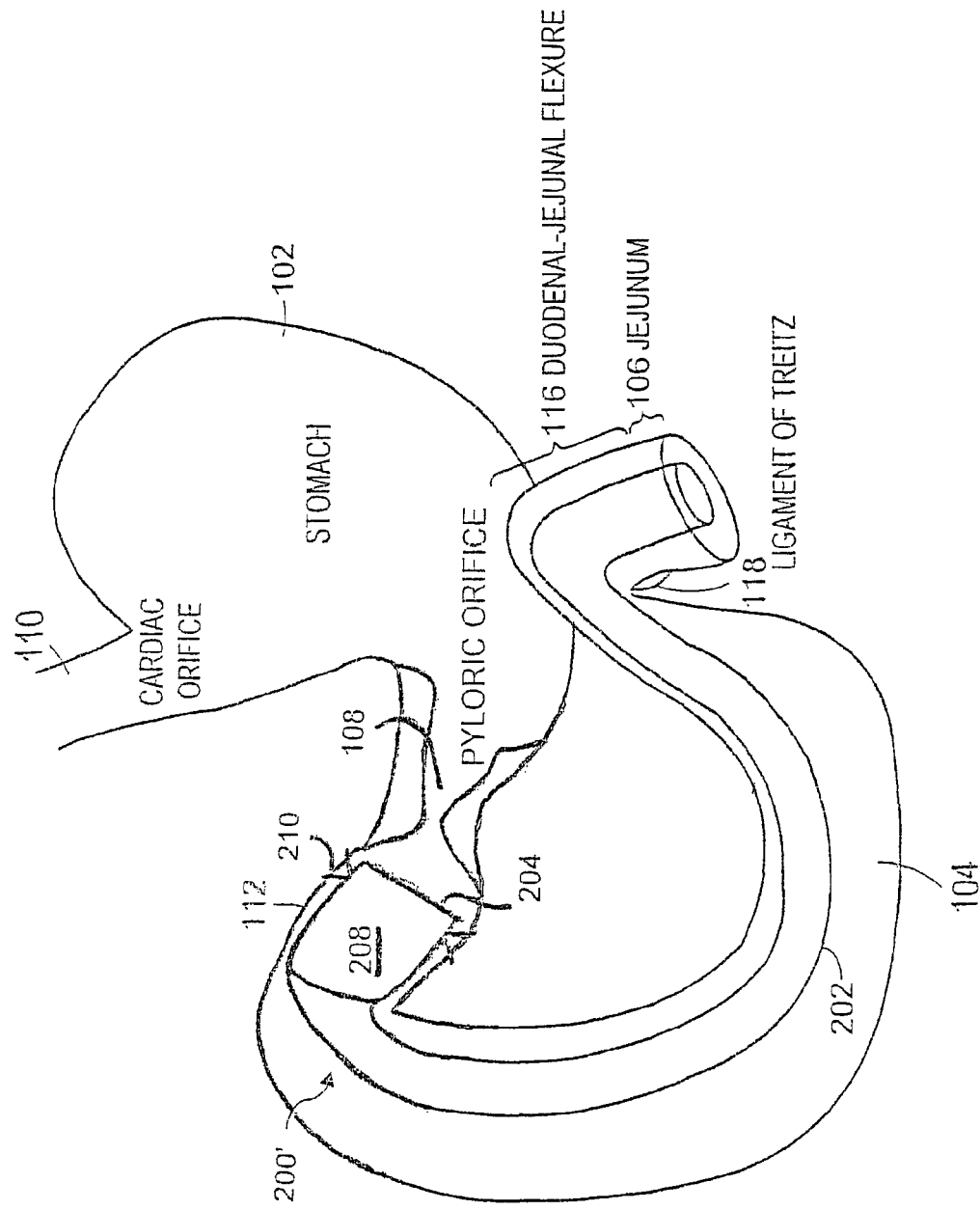
FIG. 5B is a sectional view of a body showing an alternative embodiment of the gastrointestinal implant device implanted in the digestive system.

FIG. 5A is a sectional view of a body showing one embodiment of the gastrointestinal implant device 200 implanted in the digestive system. The first proximal end 204 of the implant device 200 is anchored to muscle in the pyloric portion of the stomach 102. The barbs 210 grip onto the muscle to anchor the implant device 200 in place so that the implant device 200 can not be dragged into the stomach or down into the intestines with movement of the stomach and the intestines. FIG. 5B is a sectional view of a body showing an alternative embodiment of the gastrointestinal implant device 200' implanted distal to the pylorus 108.

The sleeve 202 extends over the ligament of Treitz 118 beyond the proximal jejunum. Extending the sleeve below the ligament of Treitz reduces the likelihood that the sleeve will move back through the duodenum 104 toward the stomach 102.

After the gastrointestinal implant device 200 has been placed in the body and anchored in either the pyloric portion of the stomach or distal to the pylorus 108, chyme leaving the stomach passes through passageway 304 (FIG. 3B) inside the sleeve 202 and bypasses the duodenum 104 and proximal jejunum 106. By directing the chyme through the sleeve 202 the digestion and the absorption process in the duodenum 104 is interrupted. By interrupting mixing of the chyme with juices in the duodenum 104, partially digested food material is not broken down into particles small enough to be absorbed by the body. Further, there is no mixing of bile with the chyme until the chyme reaches the jejunum 106. The absorption of fats and carbohydrates is reduced by delaying the mixing of bile with the chyme.

The pyloric valve opens periodically to allow chyme to exit the stomach 102 to the duodenum 104. In one embodiment of the invention the length of the stent 208 is selected to keep the pyloric valve permanently open to induce "dumping syndrome." By keeping the pylorus 108 open, the chyme empties rapidly into the sleeve 202 and passes down through the sleeve 202 and into the jejunum 106 with minimal digestion. This results in a "dumping syndrome" which is a reaction to excessive rapid dumping of chyme into the jejunum 106 causing the patient to feel ill, dizzy and nauseated. This syndrome is particularly enhanced when sugars and carbohydrates are eaten and passed directly into the jejunum 106.

To hold the pyloric valve open, the length of the stent 208 should be at least 1.5 inches so that the stent 208 extends from the anchoring position in the pyloric portion of the stomach through the pyloric orifice 108 (the opening from the stomach while the pyloric valve is open). The length of the stent is selected so that the distal end of the stent is above the papilla of vater 114 (FIG. 1). As shown, the stent 208 extends through the pyloric orifice 108 to hold the pyloric valve permanently open. In an alternative embodiment, the length of the stent 208 is selected such that the stent 208 ends at the stomach side of the pyloric orifice 108 allowing the pyloric valve to operate normally.

The sleeve 202 provides weight loss mechanisms by providing negative feedback, reduced fat digestion and reduced desire for food. The reduced fat digestion occurs because the sleeve 202 delays the mixing of bile and pancreatic juices with chyme from the stomach until after the chyme leaves the sleeve. The reduced desire for food may occur because the sleeve 202 blocks hormonal release from the duodenum.

After the chyme from the stomach has passed through the sleeve, the sleeve becomes extremely thin and floppy, permitting the sleeve to contour to the inner walls of the intestine. The sleeve is non-compliant and drapes away from the intestinal walls thereby permitting the pancreatic juice to flow unimpeded into the duodenum through the papilla of vater. The normal peristalsis of the bowel is used to propel the chyme through the intestines.

Figure 6:
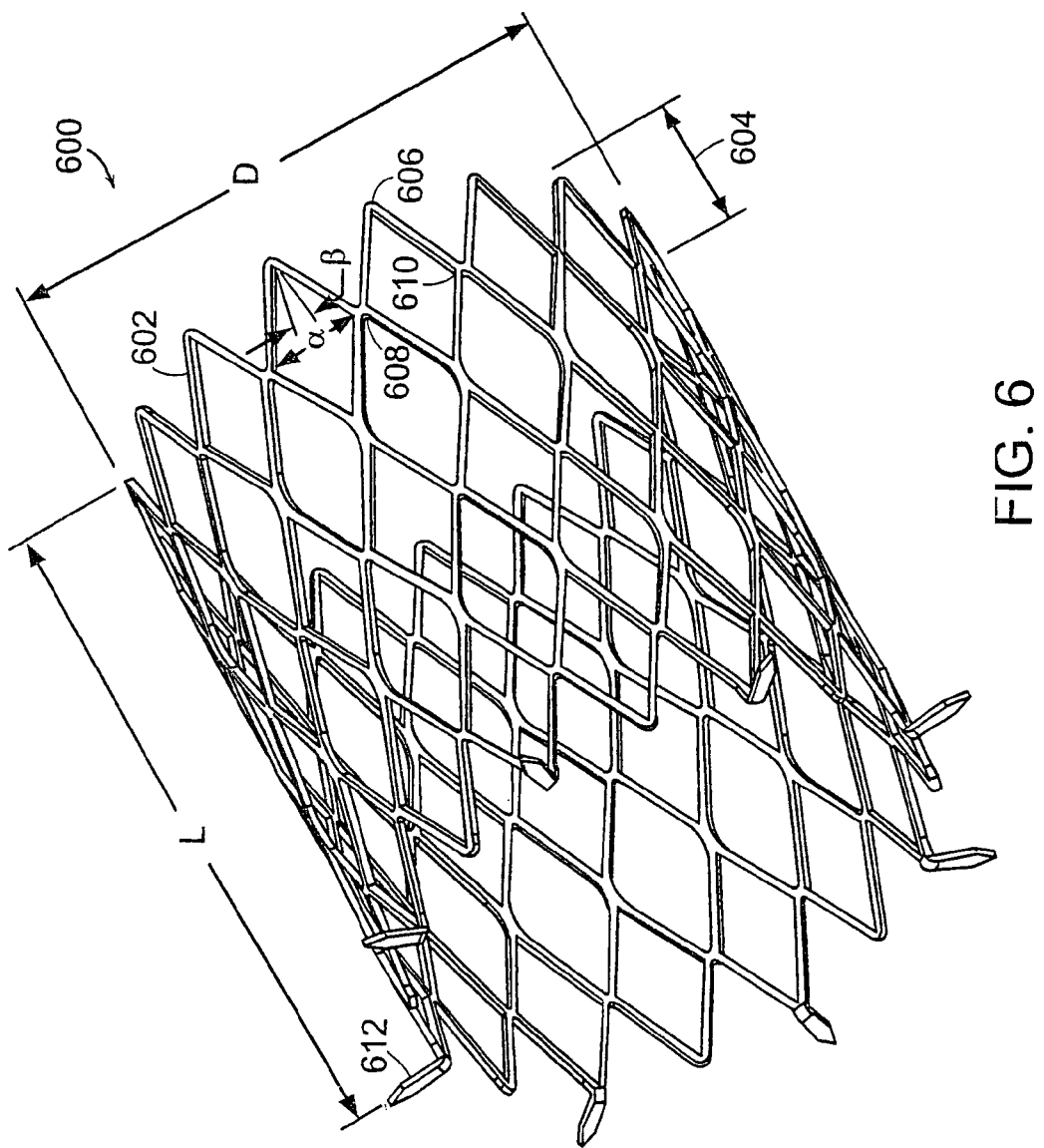
FIG. 6 is a perspective view of a collapsible self-expanding stent in the gastrointestinal implant device.

FIG. 6 is a perspective view of a collapsible self-expanding stent 600 in the gastrointestinal implant device 200 shown in FIG. 2 when expanded. The stent 600 is non-woven, collapsible and self-expanding, allowing endoscopic insertion and removal of the implant device 200. The stent 600 includes a plurality of flat struts 602 forming an open space pattern to ease collapsing while ensuring self-expansion. The open space pattern allows for collapsing into a catheter for endoscopic delivery and removal. The struts 602 may be manufactured from heat-treated spring steel such as Nitinol or MP35N.

In the embodiment shown, the stent has a length L of about 1.5 inches and has a diameter D of about 1 inch. The struts 602 are flat, about 0.010 inches wide and about 0.004 to 0.010 inches thick. The stent can be formed from a tube of material by laser cutting followed by expansion and heat setting, or other methods well known to those skilled in the art.

In an alternate embodiment, the struts 602 can be formed separately and the strut intersections can be welded or attached by other means well known to those skilled in the art. Visually the struts form sections 604 around the circumference of the stent. Each section has a series of triangles with each triangle defined by one distal strut connection 606 and two proximal strut connections 608, 610. The ratio of the collapsed diameter to the expanded diameter of the stent is roughly 1:4.

When expanded, the angle α between divergent strut sections is about 45-50 degrees and the diameter of the stent is about one inch. When compressed, the angle β between divergent strut sections is about 5-6 degrees to reduce the diameter of the stent to about 0.21 inch for endoscopic delivery and removal. The elasticity of the struts permits this compression. When the radial compression is released, the elasticity of the struts causes the stent to expand to diameter D. The stent assumes its desired diameter as the elastic restoring forces seek their minimum stress.

The ends of the struts at the proximal end of the stent 600 are elongated and shaped to provide barbs 612 to anchor to the muscle in the pyloric portion of the stomach 102.

Figure 7:
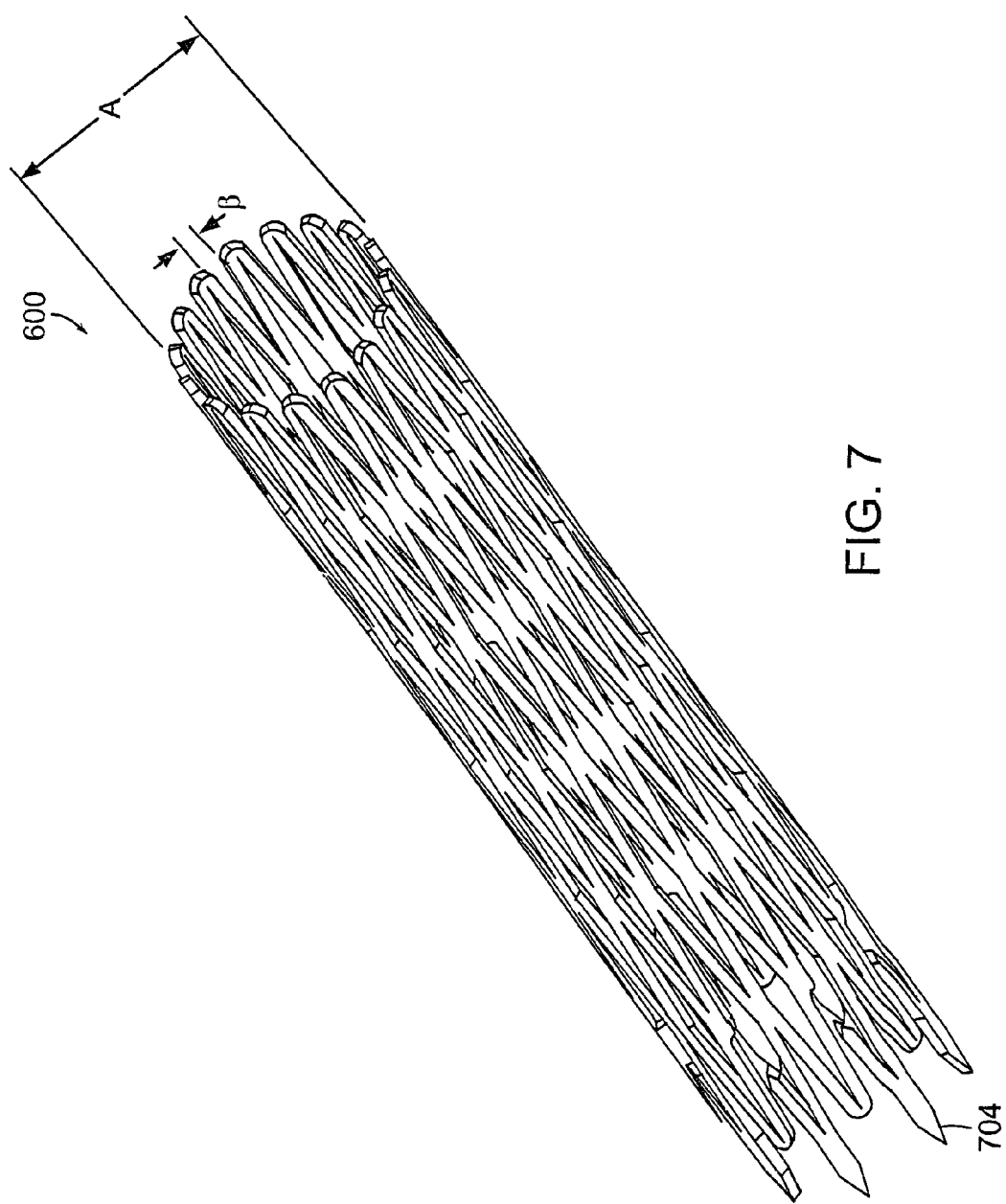
FIG. 7 is a perspective view of the stent shown in FIG. 6 when compressed.

FIG. 7 is a perspective view of the stent 600 shown in FIG. 6 when compressed. The stent 600 is compressed until the angle β between divergent strut sections is about 5-6 degrees to reduce the diameter D of the stent 600 to about 0.21 inch for endoscopic delivery and removal. The barbs 704 at the proximal end of the stent are elongated. The barbs 704 can be shaped to anchor the stent to the muscular pylorus.

Figure 8:
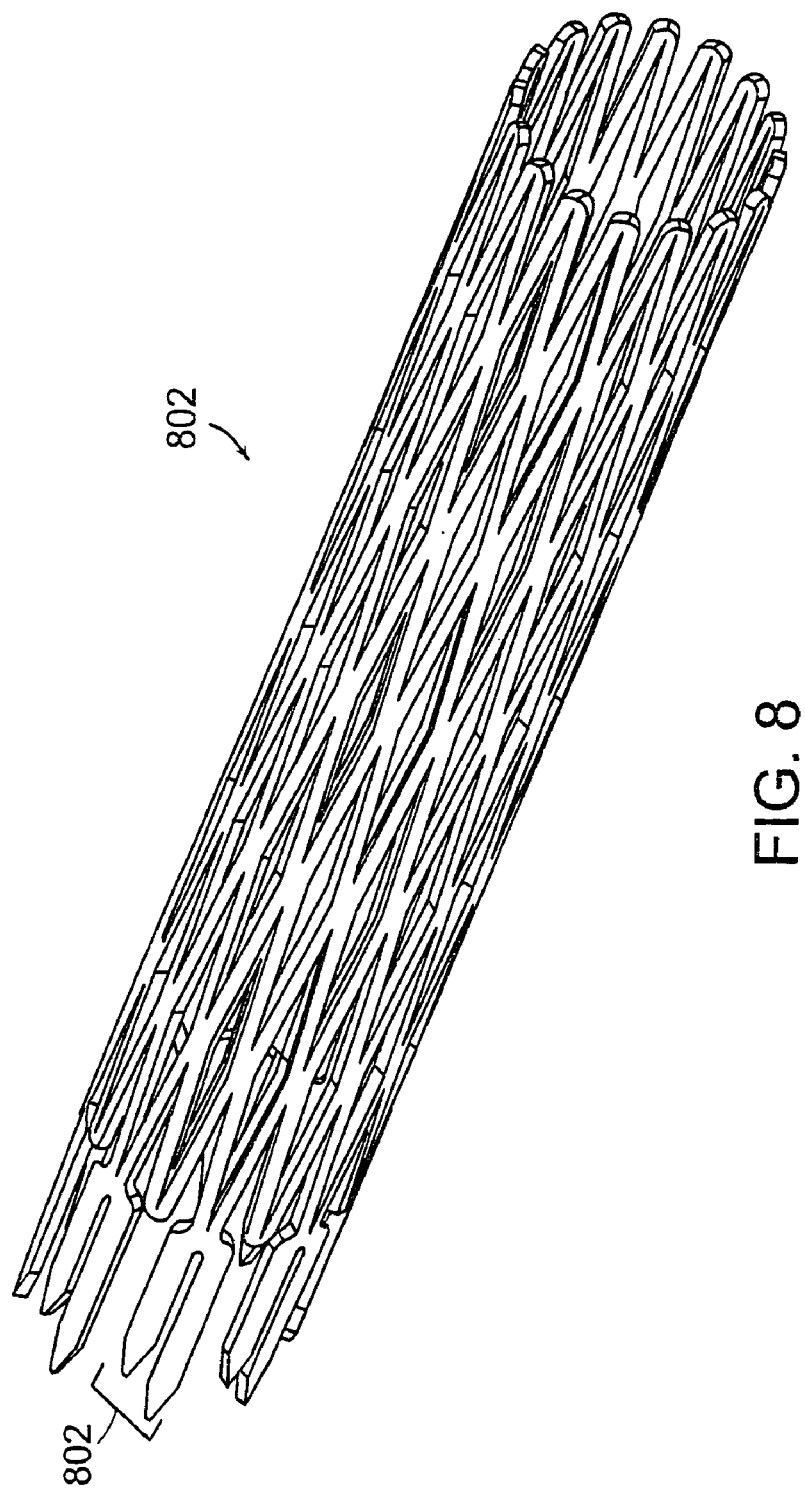
FIG. 8 is a perspective view of another embodiment of a stent when compressed.

FIG. 8 is a perspective view of another embodiment of a stent 800 when compressed. Pairs of barbs 802 at the proximal end of the stent 800 are elongated and can be shaped to provide opposed barbs to anchor the stent 800 in the muscle of the pylorus.

Figure 9:
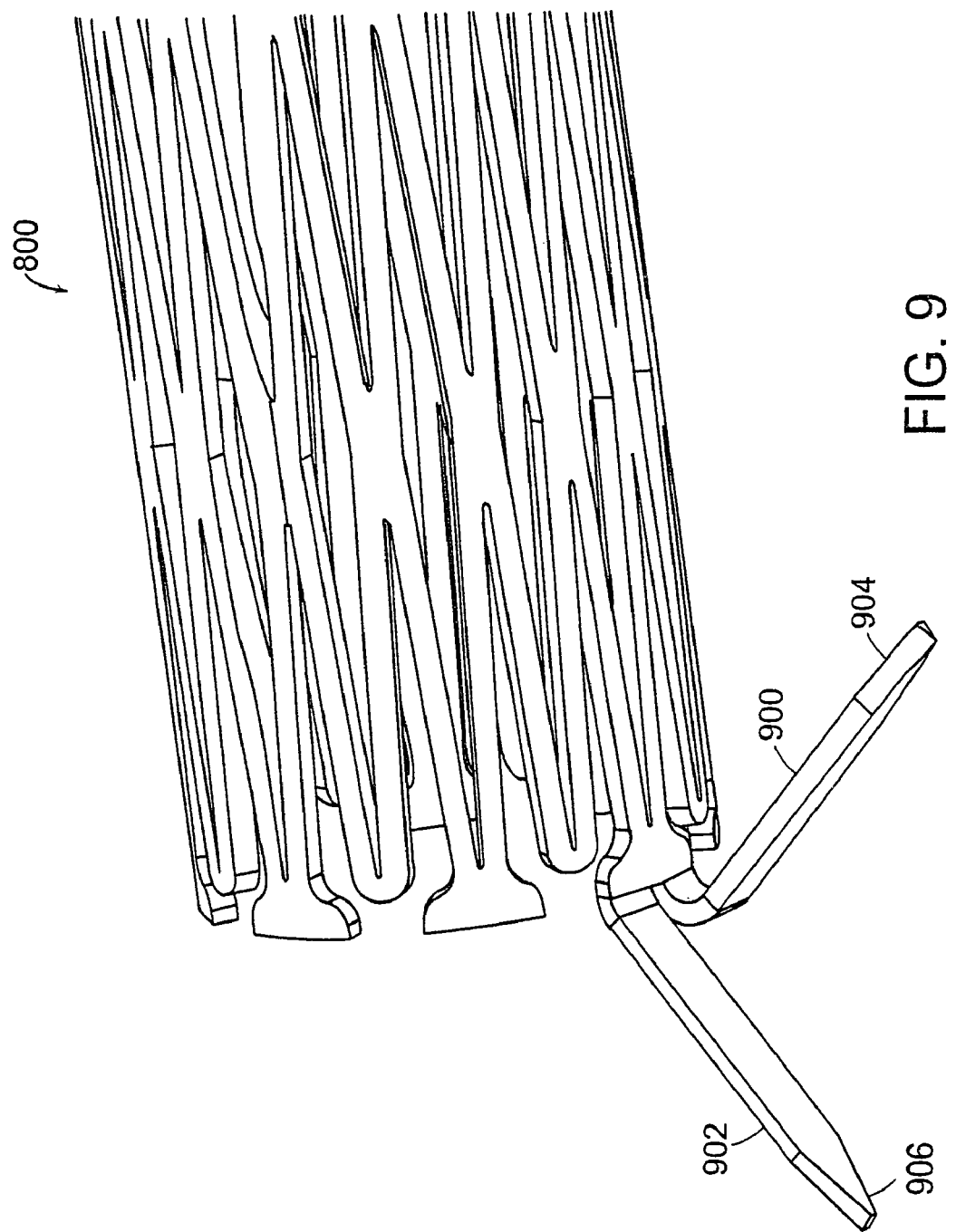
FIG. 9 is a perspective view of the stent shown in FIG. 8 with the strut ends bent to provide opposed barbs.

FIG. 9 is a perspective view of the compressed stent 800 shown in FIG. 8 with the strut ends 902, 900 bent to provide opposed barbs 904, 906. The barbs 904,906 engage the muscle of the pylorus to anchor the gastrointestinal implant device in the pylorus portion of the stomach. As shown in FIG. 2, the strut ends 900, 902 protrude outward from the outer surface of the stent 800 in opposite directions. They may be perpendicular to each other. The barbs 904, 906 at the ends of the respective opposed strut ends 900, 902 dig into the pylorus muscle to anchor the stent. The barbs 904, 906 at the end of the protruding opposed strut ends 900, 902 prevent movement of the stent 800 in either direction; that is, they prevent movement of the stent 800 into the stomach and prevent movement of the stent 800 down through the duodenum.

Figure 10:
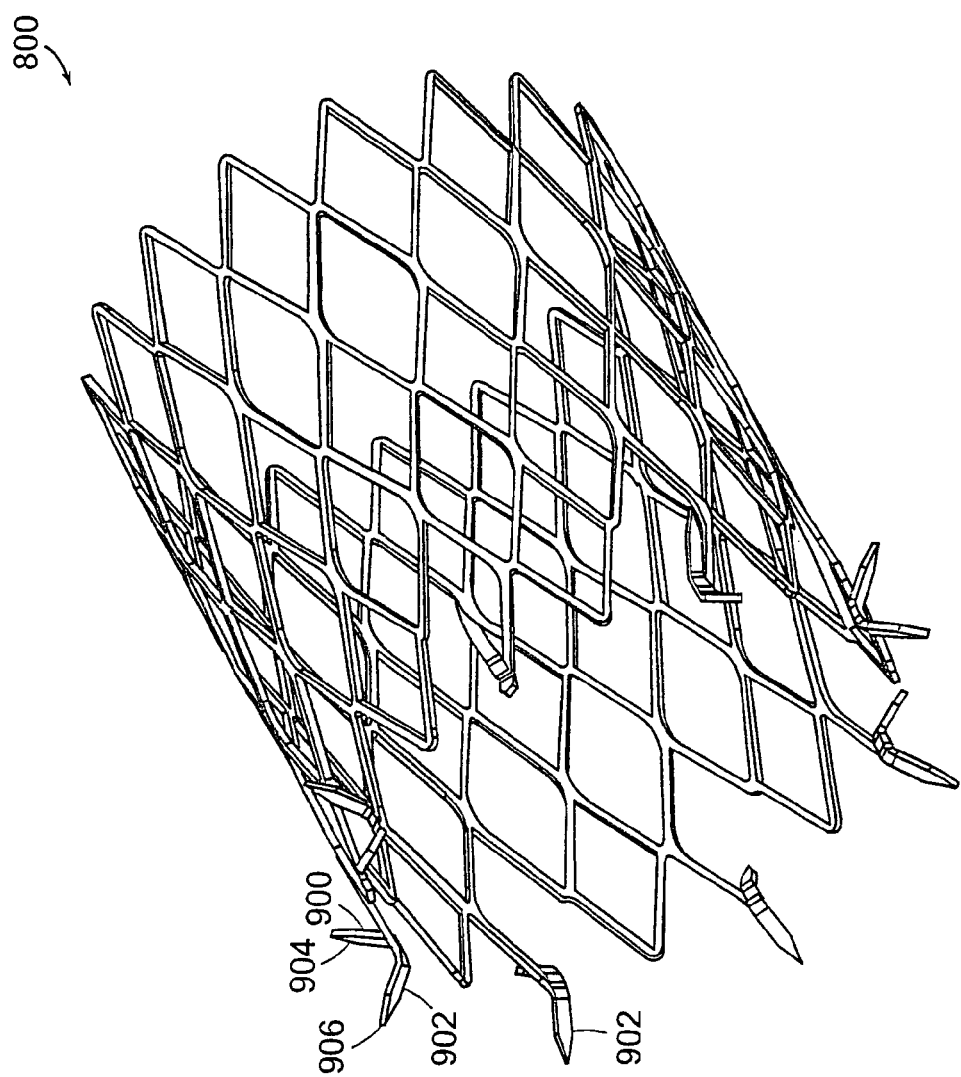
FIG. 10 is a perspective view of the stent shown in FIG. 8 when expanded.

FIG. 10 is a perspective view of the stent 800 shown in FIG. 8 when expanded. As discussed in conjunction with FIG. 9, the barbs 904, 906 engage the muscle of the pylorus while the stent 800 is expanded. In the engaged position, the barbs 904, 906 spread radially outward from the longitudinal axis of the stent 800 such that the tips of the barbs come into contact and engage the tissue.

Figure 11:
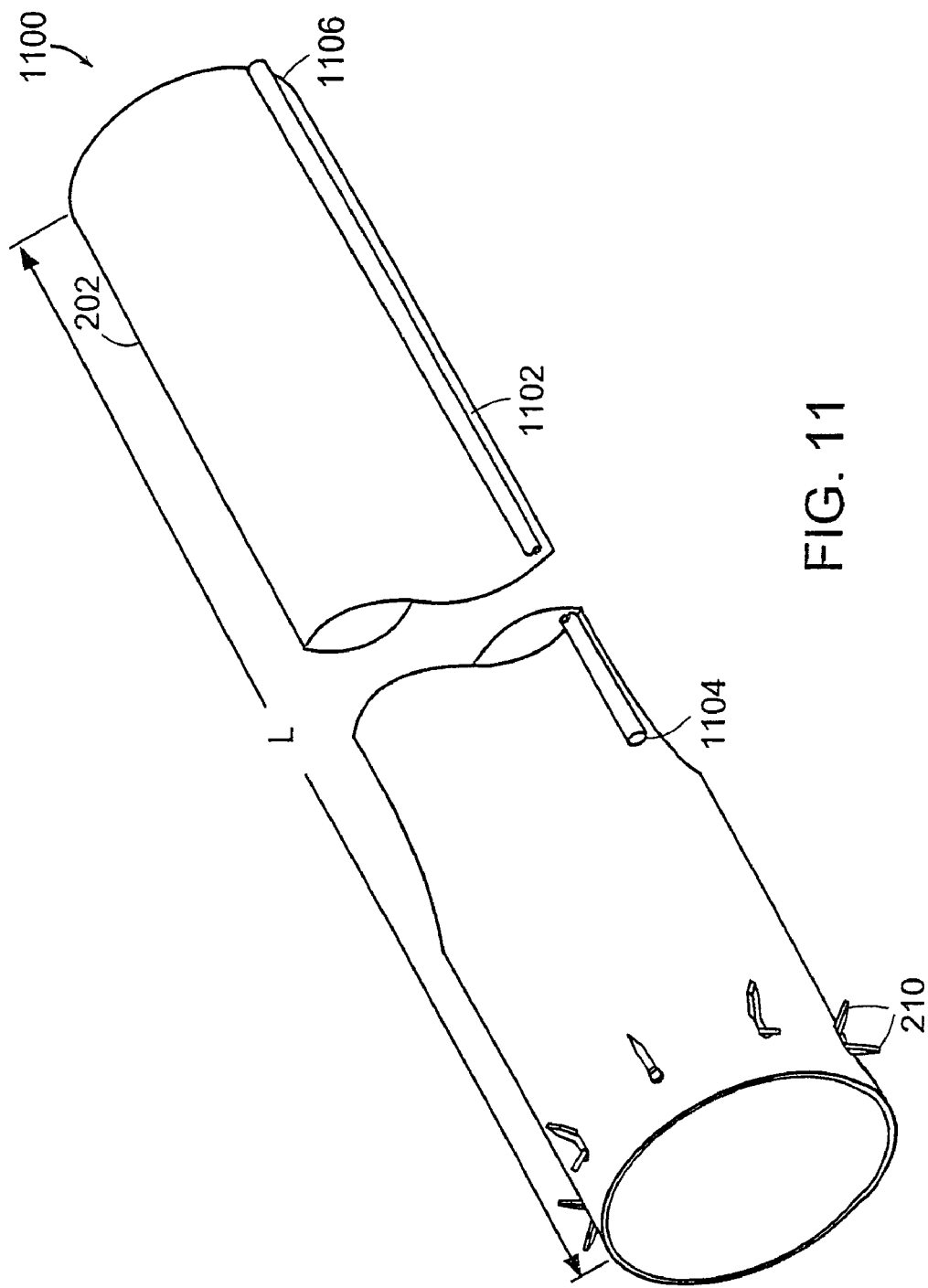
FIG. 11 illustrates the gastrointestinal device shown in FIG. 1 including an anti-buckling mechanism.

FIG. 11 illustrates the gastrointestinal device 1100 shown in FIG. 1 including an anti-buckling mechanism 1102. A flexible, anti-rotation, anti-buckling mechanism 1102 is attached to the sleeve 202 and extends from below the distal end of the stent along the length L of the sleeve to the distal end of the sleeve 202. In the embodiment shown, the anti-buckling mechanism 1102 is a guidewire device attached to the exterior surface of the outer layer of the flexible sleeve. Guidewire devices are well known to those skilled in the art. A first proximal end of the guidewire device 1104 is attached below the stent and a second distal end of the guidewire device 1106 is attached to the distal end of the flexible sleeve. The diameter of the guidewire ranges from about 0.010" to about 0.016".

The length of the sleeve 202 can be sized to just pass over the ligament of Treitz thereby bypassing only the duodenum and proximal jejunum 106. By doing this, it may not be necessary to provide any anti-buckling mechanisms in the sleeve 202 since the duodenum 104 is not very mobile compared to the jejunum 106. Typically, an anti-buckling mechanism 1102 is added to the exterior surface of a sleeve 202 having a length exceeding the length of the duodenum 104 and proximal jejunum 106.

The gastrointestinal implant device 200 is designed for endoscopic placement. FIG. 12 is a perspective view of a portion of a catheter system 1200 for delivery of the gastrointestinal implant device. The catheter system follows a guide wire 1212 through the esophagus and the stomach to the pylorus portion of the stomach. The guide wire 1212 enters a first inner lumen at the proximal end 1208 of the catheter system 1200 and exits the first inner lumen at the distal end 1222 of the catheter system 1200.

The catheter system 1200 includes an outer sheath 1202 for storing the stent 208 in collapsed form, a flange 1216 to pull back the outer sheath 1202 and a sleeve retention wire mechanism 1214 for releasing a sleeve retention wire 1210 from the proximal end of the flexible sleeve 202 after the stent has been released from the outer sheath 1202.

As described in conjunction with FIG. 2, the distal portion of the gastrointestinal implant device includes a flexible sleeve 202 which can negotiate the duodenum and the jejunum. A sleeve retention wire 1210 travels through a second inner lumen and exits the second inner lumen to secure the distal end of the sleeve 202 to an inner sheath 1226. The sleeve retention wire 1210 is coupled to the sleeve retention wire release mechanism 1214 for releasing the sleeve retention wire 1210 after the gastrointestinal implant device has been positioned in the pyloric section of the stomach. The release mechanism 1214 will be described later in conjunction with FIG. 16B.

The sleeve 202 is secured temporarily outside the inner sheath 1226 allowing for proper positioning of the gastrointestinal implant device and then for release. As shown, the sleeve 202 is secured by the sleeve retention wire 1210 using a dead-bolt mechanism 1206. Non-stick coatings such as Teflon on the sleeve retention wire 1210 are preferred to make release easier to accommodate tortuous anatomical pathways. The sleeve retention wire 1210 extends through the second inner lumen from the release mechanism 1214 of the catheter system 1200 to the dead-bolt mechanism 1206. The dead-bolt mechanism 1206 is described later in conjunction with FIG. 13A. The sleeve retention wire 1210 holds the sleeve in position. The distal end of the folded sleeve is released by the release mechanism 1214 by pulling the sleeve retention wire 1210 backward from the proximal end 1208 of the catheter.

As described in conjunction with FIG. 1, the proximal portion of the gastrointestinal device includes a covered stent. The covered stent does not enter the duodenum and thus is stiffer than the sleeve because it remains in the pylorus of the stomach. The stent in the gastrointestinal implant device is collapsed and stored in the outer lumen within the outer sheath 1202 between the flange 1216 and the distal end of the outer sheath 1202. The stent is supported in a collapsed form by the outer sheath 1202. The catheter 1200 is inserted into the digestive system through the esophagus to the pyloric section of the stomach. The proximal end of the outer sheath 1202 is positioned in the stomach, in the pylorus through the use of positioning ring 1224. After the outer sheath 1202 has been positioned, the stent is retracted from the outer lumen of the catheter by pulling flange 1216 toward the proximal end of the catheter system 1200. Upon release, the stent self-expands by its own elastic restoring force to engage the anchor portion with the stomach muscle at the pyloric section of the stomach.

Figure 14A:
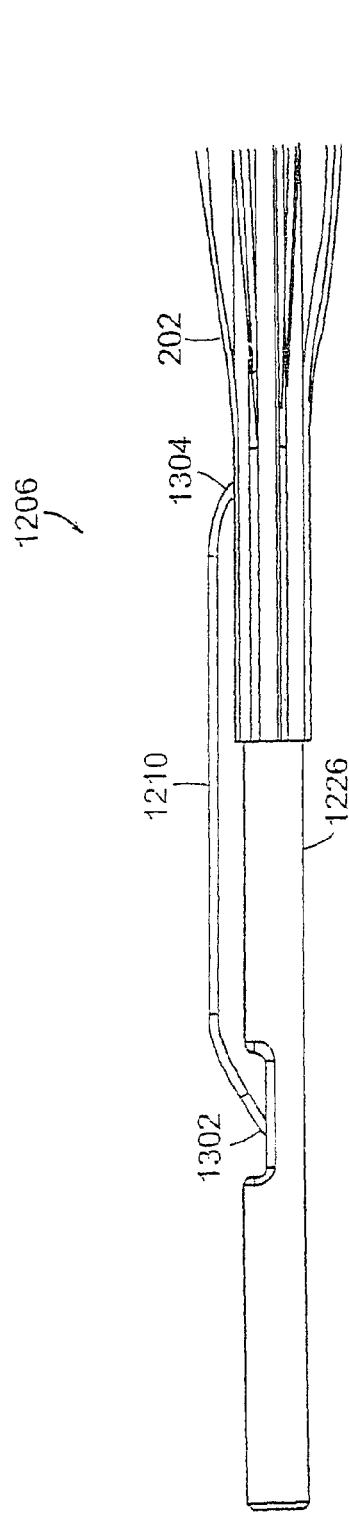
FIG. 14A is an expanded perspective view of the dead-bolt mechanism shown in FIG. 12.

FIG. 13 is a cross-sectional view of the inner shaft 1226 taken along line E-E of FIG. 12. The sleeve retention wire 1210 passes through a second inner lumen 1314 in the inner sheath 1226. The sleeve retention wire 1210 exits the second inner lumen 1314 and is threaded through folds of the sleeve 202 at 1302 in FIG. 14A. The sleeve retention wire 1210 re-enters the second inner lumen 1314 at 1302 (FIG. 14A). The guidewire 1212 passes through the first inner lumen 1310.

FIG. 14A is an expanded perspective view of the dead-bolt mechanism 1206 shown in FIG. 12. The sleeve 202 has been folded for delivery. The sleeve is wrapped around the inner sheath 1226 and bunched above the inner sheath 1226 The sleeve is held in folded position around the inner sheath 1226 by threading the sleeve retention wire 1210 through the folds of the sleeve 202. The sleeve retention wire 1210 exits the second inner lumen 1314 through an opening 1306 and pierces through folds of the sleeve 202 at 1304. Threading the sleeve retention wire 1210 through the folds of the sleeve 202 results in a plurality of small holes at the distal end of the sleeve 202. The holes are reinforced with silicone or urethane to avoid tears in the material. The sleeve retention wire 1210 re-enters the second inner lumen through a second hole 1302 and advances a sufficient distance within the second inner lumen toward the distal end of the second inner lumen to resist pulling out of the second inner lumen.

Figure 14B:
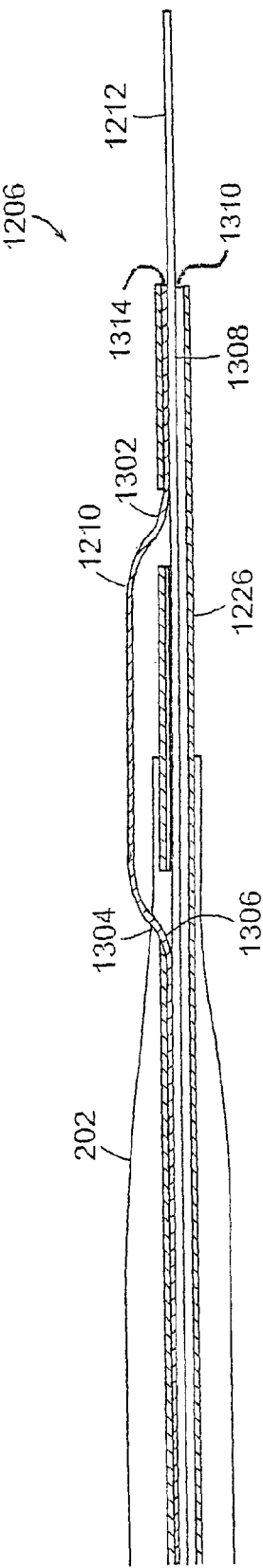
FIG. 14B is a sectional view of the dead-bolt mechanism shown in FIG. 13A illustrating the sleeve retention wire threaded through the sleeve.

FIG. 14B is a sectional view of the dead-bolt mechanism 1206 shown in FIG. 14A illustrating the sleeve retention wire 1210 threaded through the sleeve. The sleeve retention wire 1210 exits the second inner lumen 1314 at 1306 and pierces through folds in the sleeve 202 at 1304. The sleeve retention wire 1210 re-enters the second inner lumen 1314 at 1302.

Figure 15:
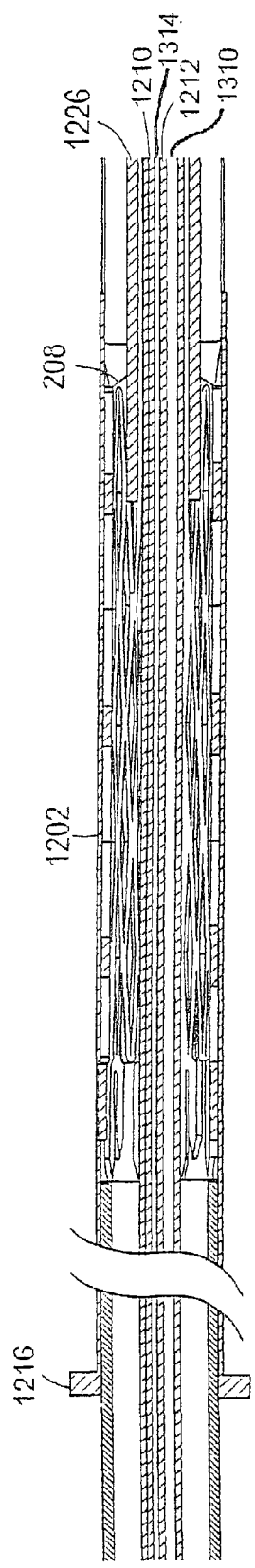
FIG. 15 is sectional view of a portion of the catheter system illustrating the collapsed stent stored inside the outer sheath.

FIG. 15 is a sectional view of a portion of the catheter system shown in FIG. 12 illustrating the collapsed stent 208 stored inside the outer sheath 1202. The stent 208 is pre-compressed and held in a collapsed form inside the outer sheath 1202 of the catheter. The outer sheath 1202 is pulled back by the flange 1216 toward the proximal end of the catheter system 1200 to release the self-expanding stent 208. The stent radially expands under its own elastic restoring force. The guidewire 1212 is directed through the first inner lumen 1310 and the sleeve retention wire 1210 is directed through the second inner lumen in the inner sheath 1226. The inner sheath includes a first lumen through which the guidewire passes and a second lumen through which the sleeve retention wire passes.

Figure 16A:
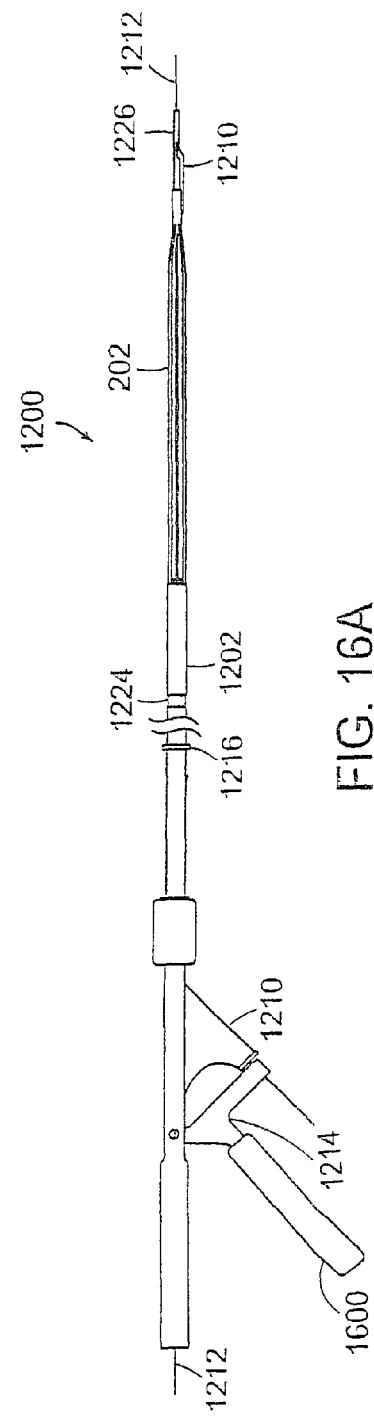
FIG. 16A is a plan view of the catheter system illustrating the collapsed stent stored inside the outer sheath of the gastrointestinal implant device.

FIGS. 16A-C illustrate a method for delivery of the gastrointestinal implant device. FIG. 16A is a plan view of the catheter system illustrating the collapsed stent stored inside the outer sheath 1202 of the gastrointestinal implant device. As described in conjunction with FIG. 12, the stent 208 is stored inside the outer sheath and the distal end of the sleeve 202 is secured outside the inner sheath 1226 by a sleeve retention wire 1210.

FIG. 16B is a plan view of the catheter system 1200 illustrating the gastrointestinal implant device after release of the stent 208 from the outer sheath 1202. The flange 1216 has been pulled back toward the proximal end of the catheter system 1200 to pull back the outer sheath 1202 from the stent and the stent 208 has self-expanded. The sleeve retention wire 1210 holds the distal end of the sleeve 202.

Once in place, the sleeve retention wire 1210 can be removed. As described previously in conjunction with FIG. 12, the sleeve retention wire 1210 is coupled to locking mechanism 1224. Handle 1600 in the locking mechanism 1214 acts as a pivot device to pull the sleeve retention wire 1210 from the dead-bolt mechanism 1206. The distal end of the gastrointestinal implant device is released by moving handle 1600 in a clockwise direction 1604. As the handle 1600 is moved in direction 1604, the sleeve retention wire 1210 threaded through the folds of the sleeve is pulled back through the second inner lumen 1314 and disengages from the sleeve at the distal end of the gastrointestinal implant device. The sleeve retention wire 1210 extends from the distal end of the gastrointestinal implant device through the second inner lumen 1314. The wire is connected to the handle 1600 at the proximal end of the catheter.

FIG. 16C is a plan view of the catheter system illustrating the expanded gastrointestinal implant device after the sleeve retention wire has been released. The handle 1600 has been moved in a clockwise direction and the sleeve retention wire 1210 has been pulled back through the second inner lumen 1314 to release the distal end of the sleeve 202.

Figure 17:
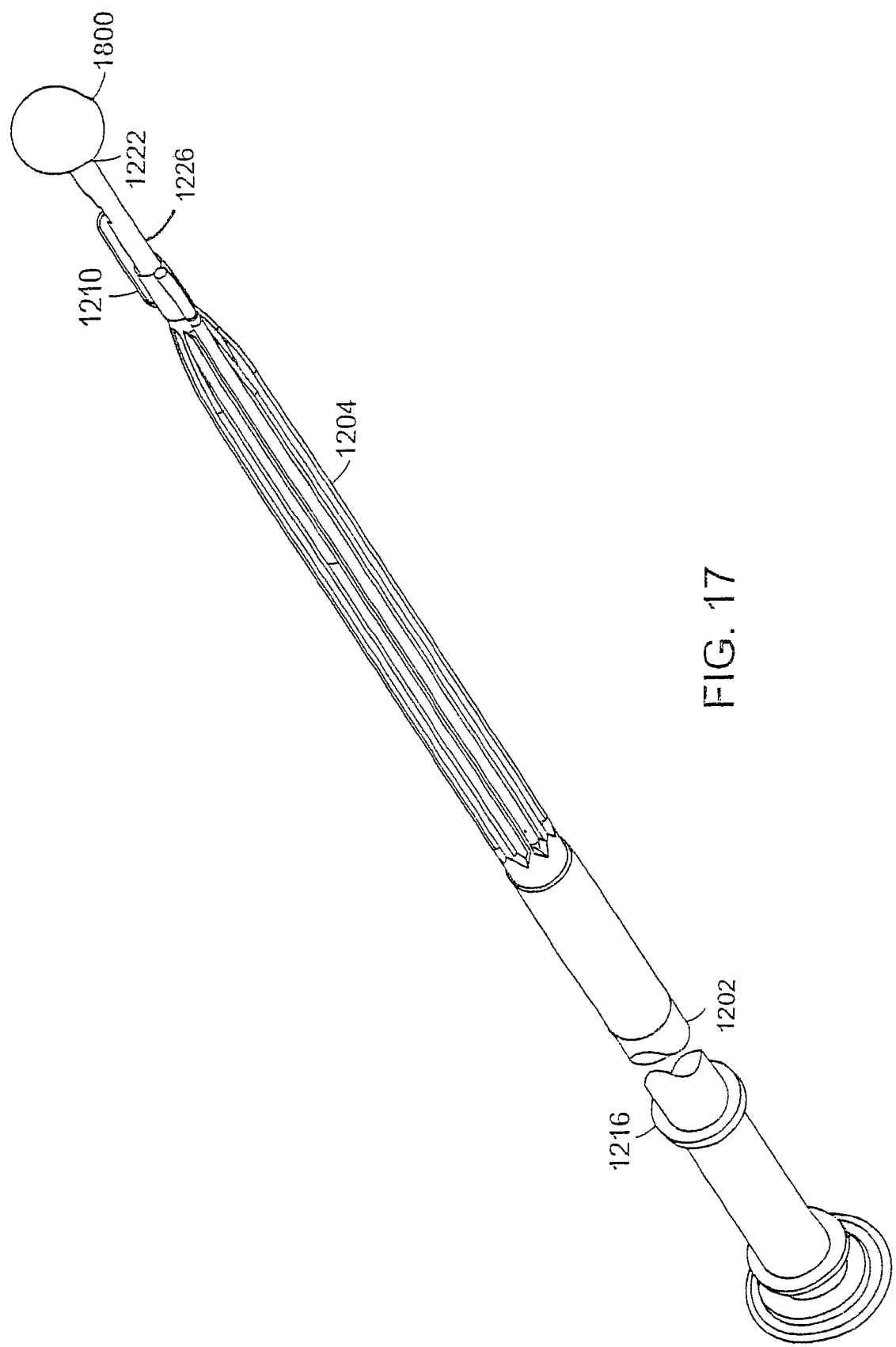
FIG. 17 is a perspective view of another embodiment of the catheter system shown in FIG. 12.

FIG. 17 is a perspective view of another embodiment of the catheter system shown in FIG. 16. The catheter includes a ball 1800 coupled to the distal end 1222 of the inner sheath 1226 for guiding the catheter through the alimentary canal (e.g., to the pyloric portion of the stomach). The ball 1800 is small enough so that it can be pulled back through the gastrointestinal implant device after the gastrointestinal device has been delivered, the stent expanded and the sleeve retention wire 1210 has been released. The sleeve is shown uniformly folded 1204. However, the sleeve may not necessarily be uniformly folded.

Figure 18:
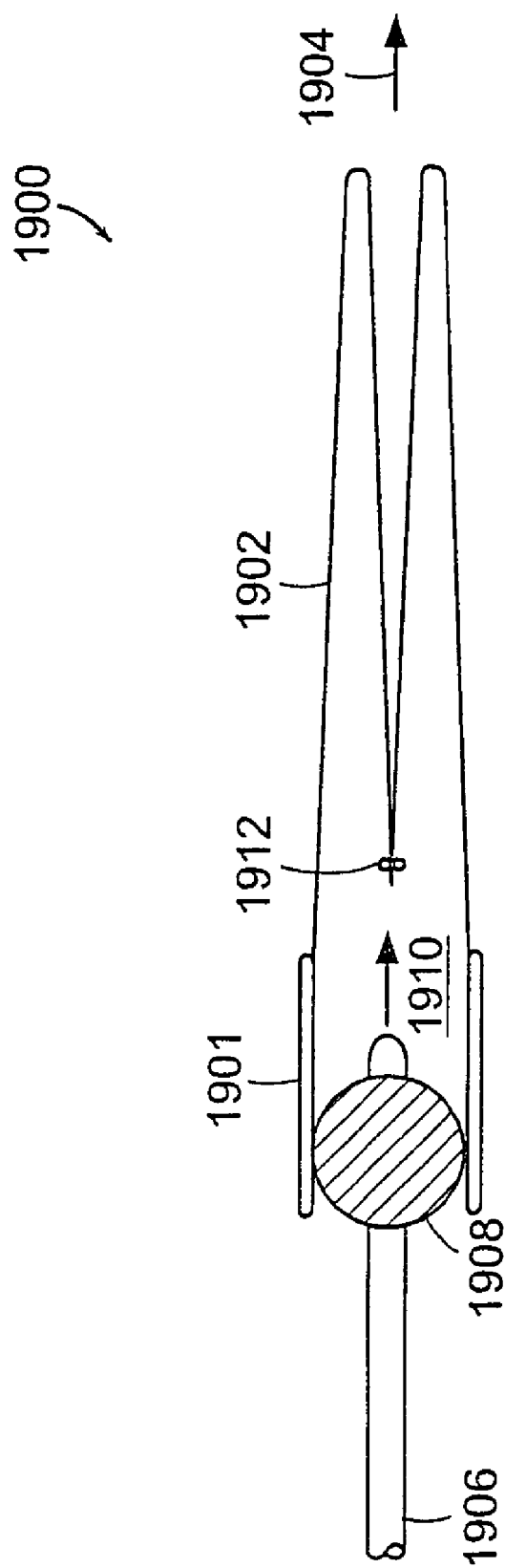
FIG. 18 is a sectional view of an everting catheter system for delivery of a longer length sleeve.

FIG. 18 is a cross-section of an everting catheter system 1900 for delivery of a longer flexible sleeve. The gastrointestinal implant device 200 is shown with the stent sleeve anchor 1901 and the attached sleeve 1902 shown as delivered into the anatomy. The delivery catheter previously described is then removed. A balloon catheter 1906 is introduced into the stent sleeve anchor 1901 and the balloon 1908 inflated to seal the lumen of the stent 1901. The sleeve 1902 is folded inside itself and an elastic band 1912 is used to seal the end of the sleeve. Fluid is then injected through the balloon catheter shaft 1906 into the sleeve lumen 1910, filling the lumen and pressurizing it. The pressure of the fluid is used to push the inner sleeve distally towards 1904. When the sleeve 1902 has fully deployed distally, the elastic band 1912 falls off of the closed end of the sleeve 1902 and passes distally in the intestine until it is excreted. This mechanism permits deployment of a sleeve that is double the length of the delivered device. This may be needed as it is difficult to access the distal parts of the intestine with guidewires. This everting catheter system enables delivery of longer sleeves than are possible using only the delivery catheter described in conjunction with FIG. 12.

Figure 19:
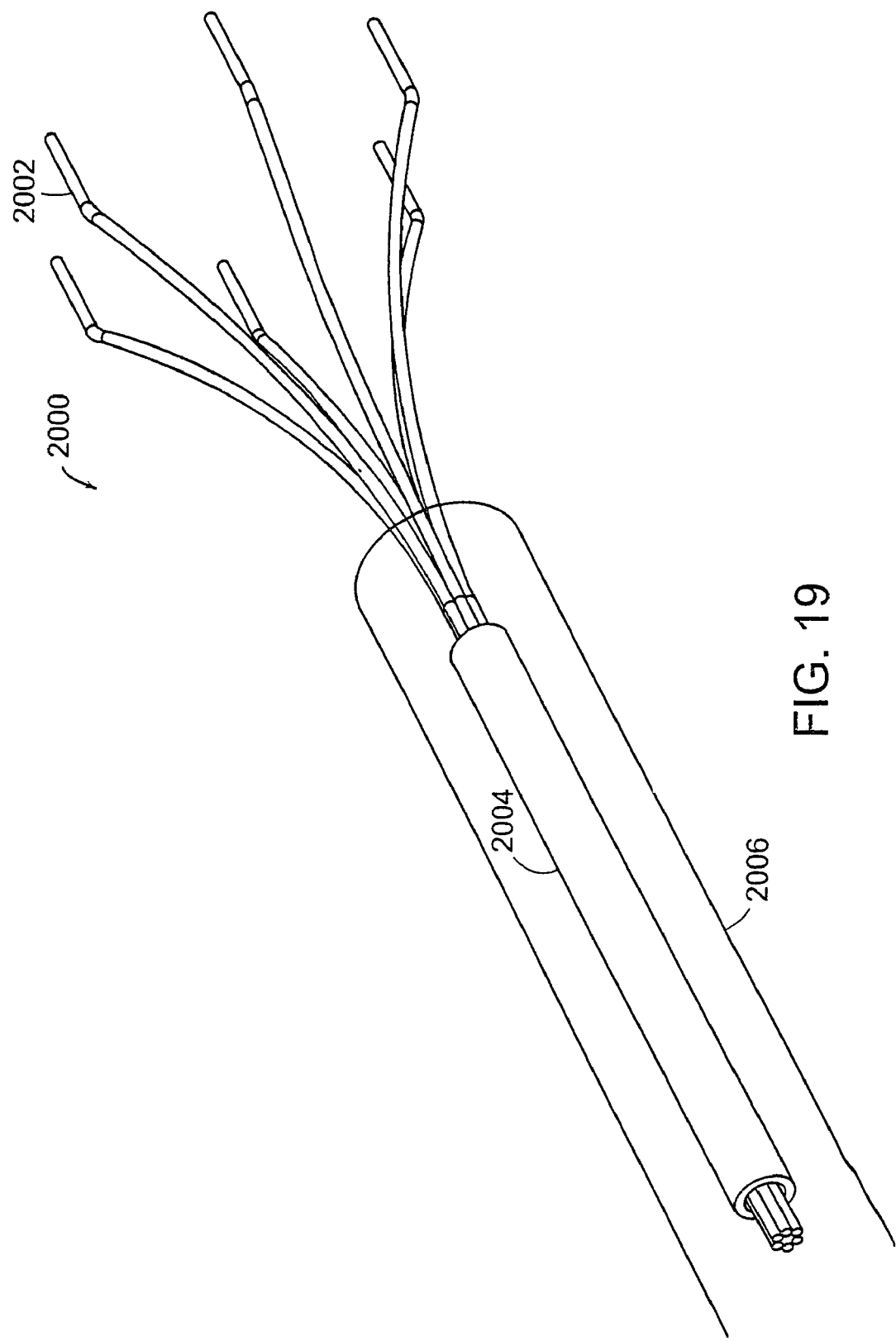
FIG. 19 is a perspective view of a retrieval device for removing the gastrointestinal implant device from the digestive tract.

FIG. 19 is a perspective view of a retrieval device 2000 for removing the gastrointestinal implant device 200 from the digestive tract. As already described, the exterior surface of the stent 208 is covered with a material that prevents cellular in-growth allowing the stent 208 to be easily removed. The retrieval device 2000 includes an inner sheath 2004 and an outer sheath 2006. A plurality of fingers 2002 extend from the proximal end of the inner sheath 2004. The fingers 2002 engage the exterior surface of the gastrointestinal device. As the inner sheath 2004 is moved down over the fingers, the fingers 2002 pull radially inward to reduce the proximal stent diameter and pull the collapsed device into the outer sheath 2006.

Figure 20:
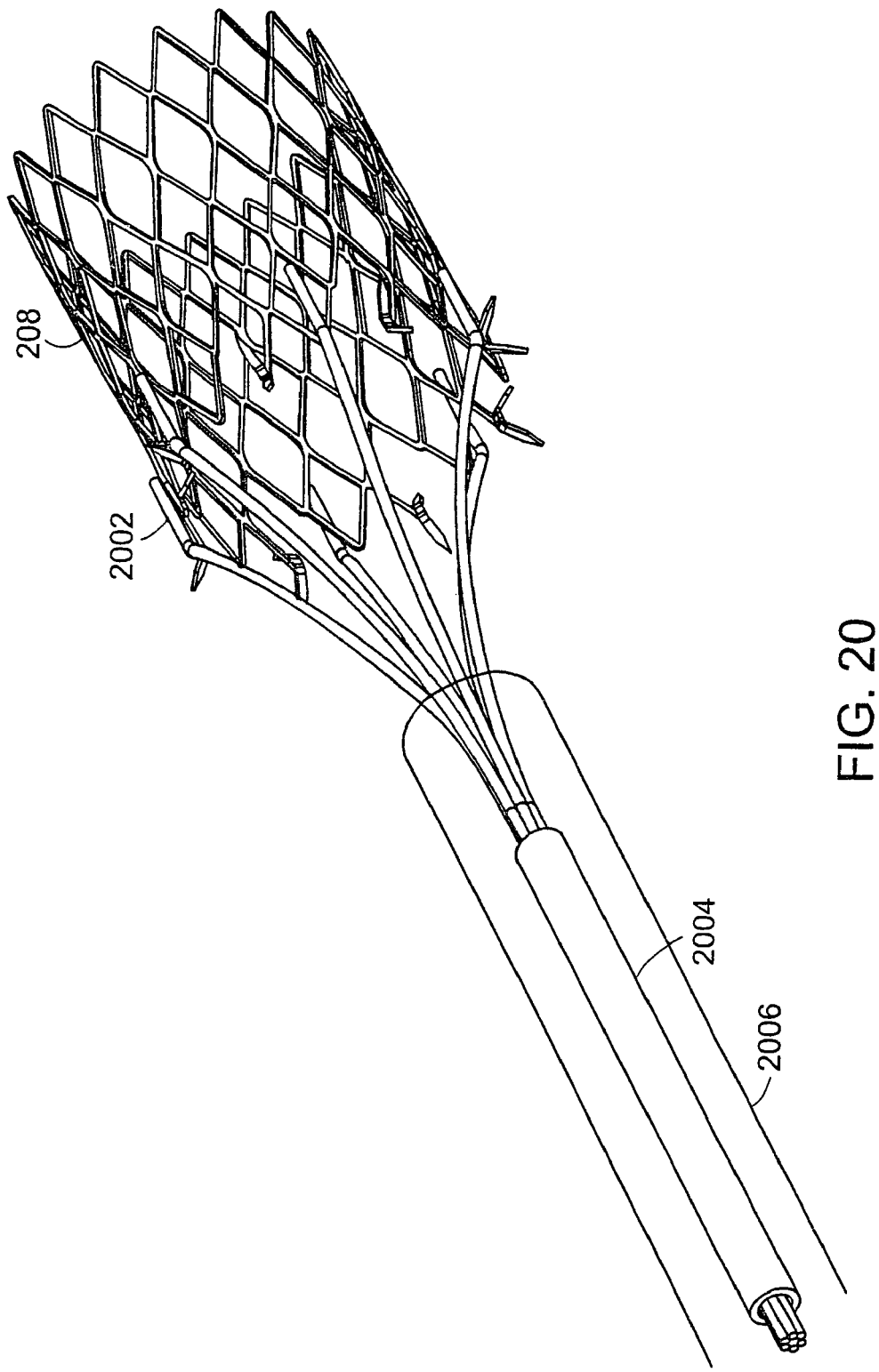
FIG. 20 is a perspective view of the removal device engaged with the stent.

FIG. 20 is a perspective view of the retrieval device 2000 engaged with the stent 208. The fingers 2002 of the retrieval device are positioned around the stent 208. As the inner sheath 2004 is pushed over the fingers 2002, the fingers pull radially inward on the proximal end of the stent 208 and the proximal end of the stent 208 is collapsed. After the stent 208 has been collapsed sufficiently such that the proximal stent diameter is less than the diameter of the outer sheath 2006, the stent is drawn into the outer sheath 2006. The entire gastrointestinal implant device can then easily be removed from the patient by pulling retrieval device 2000 through the stomach and the esophagus.

Figure 21:
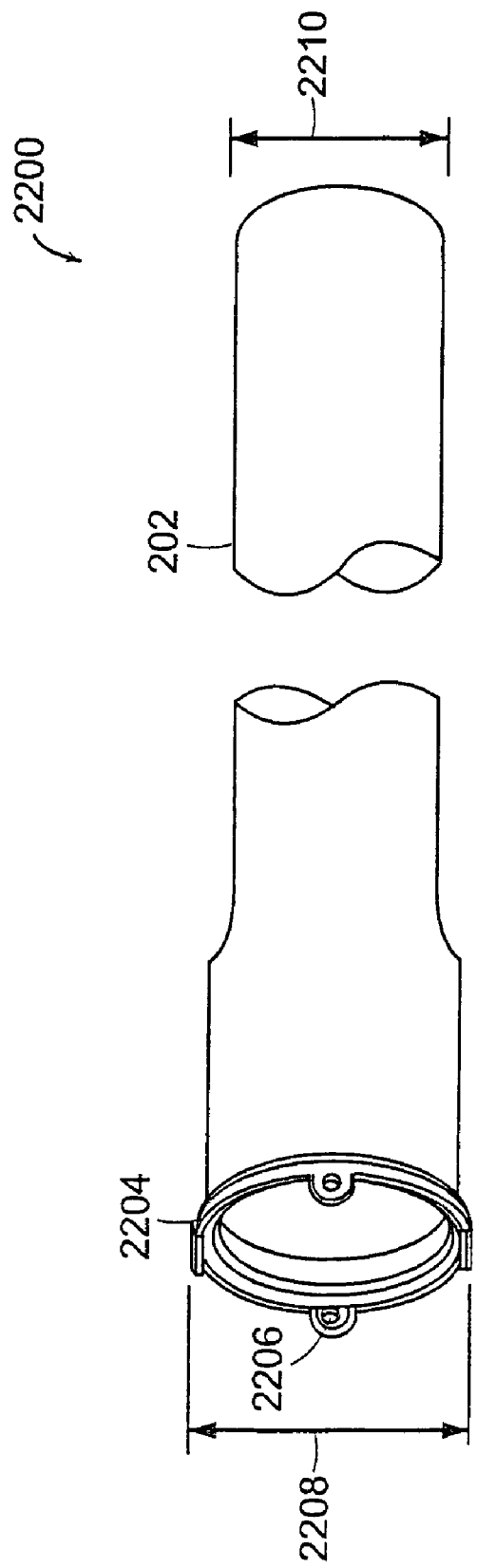
FIG. 21 is a perspective view of another embodiment of a gastrointestinal implant device.

FIG. 21 is a perspective view of another embodiment of a gastrointestinal implant device 2200. The gastrointestinal implant device 2200 includes a sleeve 202 and an anchoring ring 2204. The distal end of the anchoring ring 2204 is bonded to the proximal end of the sleeve 202. A plurality of eyelets 2206 are distributed around the circumference of the proximal end of the ring for anchoring the device to the pyloric muscle using anchors shown in FIG. 24. The anchoring ring 2204 is made from a flexible material such as silicone allowing the ring 2204 to be collapsed for endoscopic insertion and removal.

The anchoring ring 2204 does not hold the pylorus open. However, in an alternate embodiment, the anchoring ring 2204 can be bonded to a stent with sufficient length and diameter to hold the pylorus open as described in conjunction with FIG. 2. The anchoring ring 2204 anchors the device and the stent holds the pylorus open.

Figure 22:
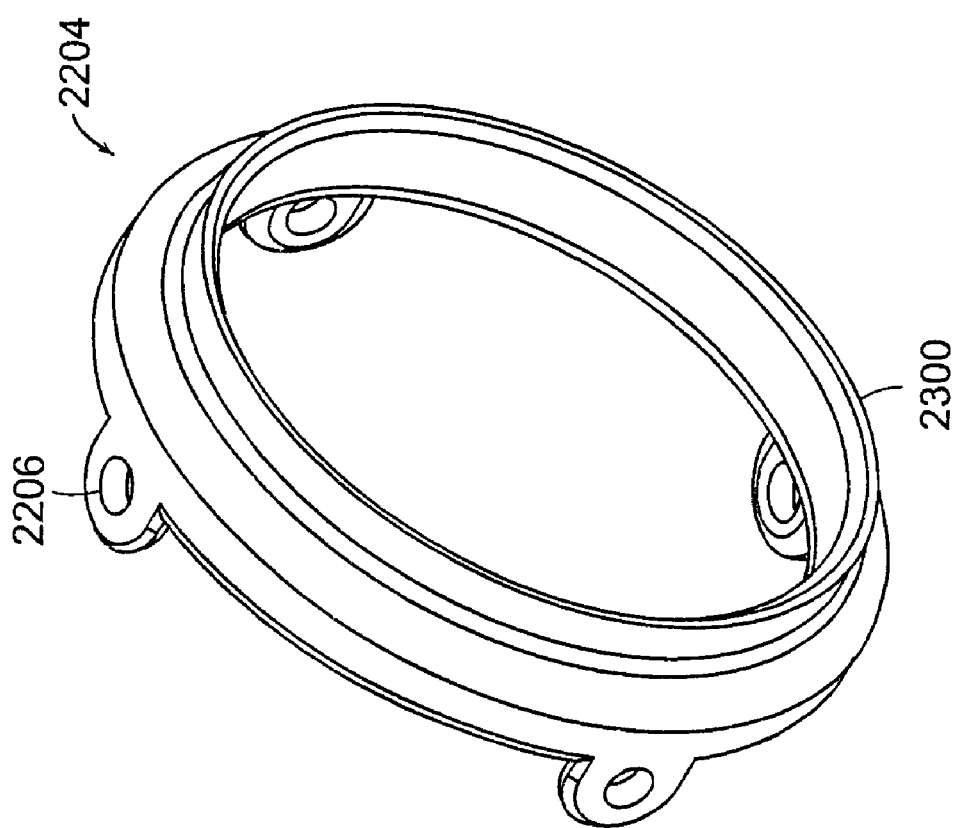
FIG. 22 is a perspective view of the anchoring ring shown in FIG. 21.

FIG. 22 is a perspective view of the anchoring ring 2204 shown in FIG. 21 in the expanded position. The sleeve is bonded to the outer surface 2300 of the proximal end of the anchoring ring whose diameter is 0.8" or about the same as the diameter of the sleeve. The anchoring ring 2204 includes at least four eyelets to anchor the device in place. The outer most diameter of the ring is about one inch. In an alternate embodiment there can be more than four eyelets.

Figure 23:
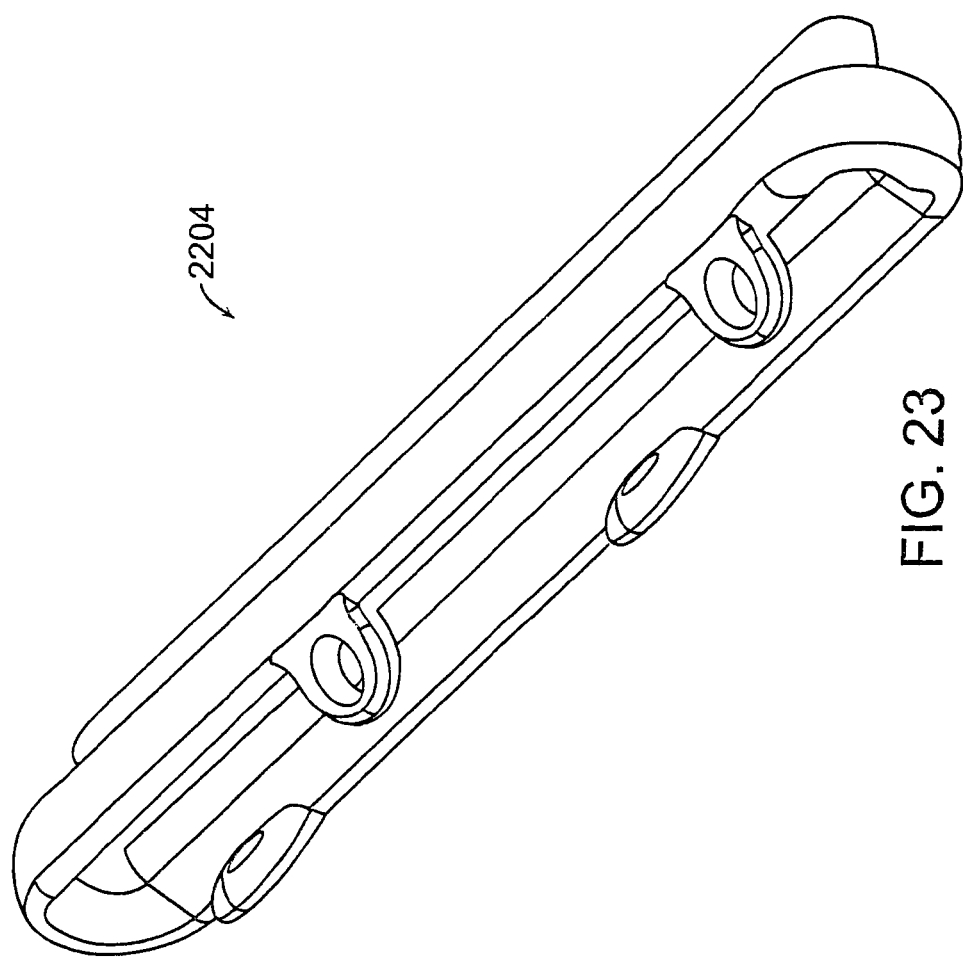
FIG. 23 is a perspective view of the anchoring ring shown in FIG. 21 in a collapsed position for insertion and removal.

FIG. 23 is a perspective view of the anchoring ring 2204 shown in FIG. 21 in a collapsed position for insertion and removal. The circular ring 2204 shown in FIG. 21 has been compressed to an oval shape allowing the anchoring ring to be inserted into the lumen of a catheter for delivery.

Figure 24:
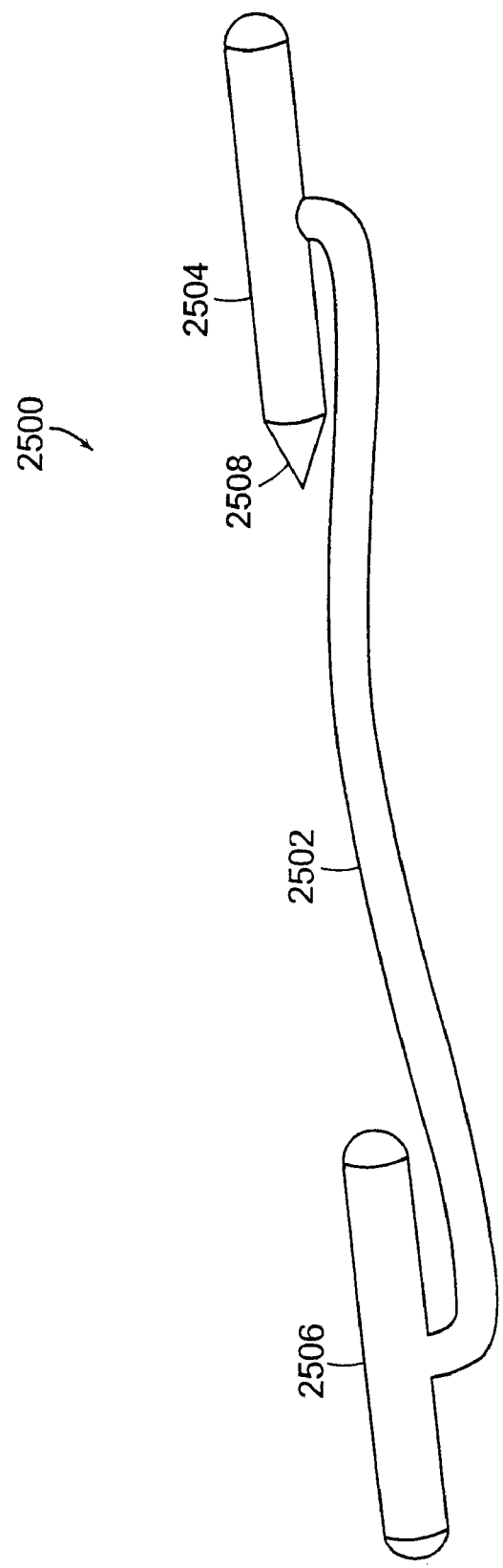
FIG. 24 is a perspective view of an anchor for anchoring the collapsible ring shown in FIG. 23 to the muscular tissue of the pyloric section of the stomach.

FIG. 24 is a perspective view of an anchor 2500 for anchoring the collapsible ring shown in FIG. 23 to the muscular tissue of the pyloric orifice. The anchor 2500 includes an anchor pin 2504 coupled to a second pin 2506 by a flexible shaft 2502. The anchor pin 2504 includes a shaped barb 2508 for locking the anchor 2500 into the tissue. The anchor 2500 is delivered after the collapsible ring has been positioned in the pyloric orifice. The anchor is guided so that the anchor pin 2504 is directed through a respective eyelet with the barbed portion of the anchor pin 2504 guided toward the tissue. After the barb 2508 has been locked into the tissue, the second pin 2506 sits inside the gastrointestinal implant device while the barbed portion 2508 of the anchor pin 2504 sits inside the pylorus muscle tissue. For removal of the gastrointestinal implant device from the body, the flexible shaft 2502 of the anchor 2500 is cut.

FIG. 25A is a perspective view of a delivery system 2600 for delivering the anchor 2500 after the gastrointestinal implant device has been placed in the pyloric orifice. The anchor 2500 is loaded in the distal end of a catheter having a single lumen tube 2600. The hollow, distal end of the delivery device is a sharp needle made to penetrate the pylorus muscle. In an alternate embodiment, the distal end of the delivery device can be formed in an arc to improve access to the eyelets 2206 through an endoscopic approach. The catheter 2600 includes a pusher 2604 for releasing the anchor 2500. The pusher 2604 is moved in a longitudinal direction 2602 to release the anchor 2500 from the lumen.

FIG. 25B is a plan view of the delivery system 2600 shown in FIG. 25A. FIG. 25C is a cross-sectional view of the distal end of the catheter 2600 as taken along line B-B of FIG. 25B. As described in conjunction with FIG. 24, the anchor 2500 includes pins 2504, 2506 coupled by a flexible shaft 2502. The anchor 2500 is loaded in the lumen at the distal end of the catheter 2600. The anchor pin 2504 is placed in the distal end of the tube 2600 and the second pin 2506 in the proximal end. The barb 2508 on the anchor pin 2504 is pointed toward the proximal end of the tube 2506 to engage with the tissue upon release in the muscle tissue. The catheter is advanced to the center of the ring positioned in the pyloric orifice. The sharp end 2510 is then pushed through an eyelet and into the muscle tissue. The pusher 2506 is pushed in longitudinal direction 2602 to release the distal anchor 2506. Once the distal anchor is released, the delivery system is pulled back, dragging the proximal part of the anchor out of the delivery device with the flexible shaft going through the eyelet, and the proximal anchor portion resting on the inside of the device. In the embodiment of the ring shown in FIG. 22, four anchors 2506 are delivered to anchor the gastrointestinal implant device through the four eyelets.

Figure 25D:
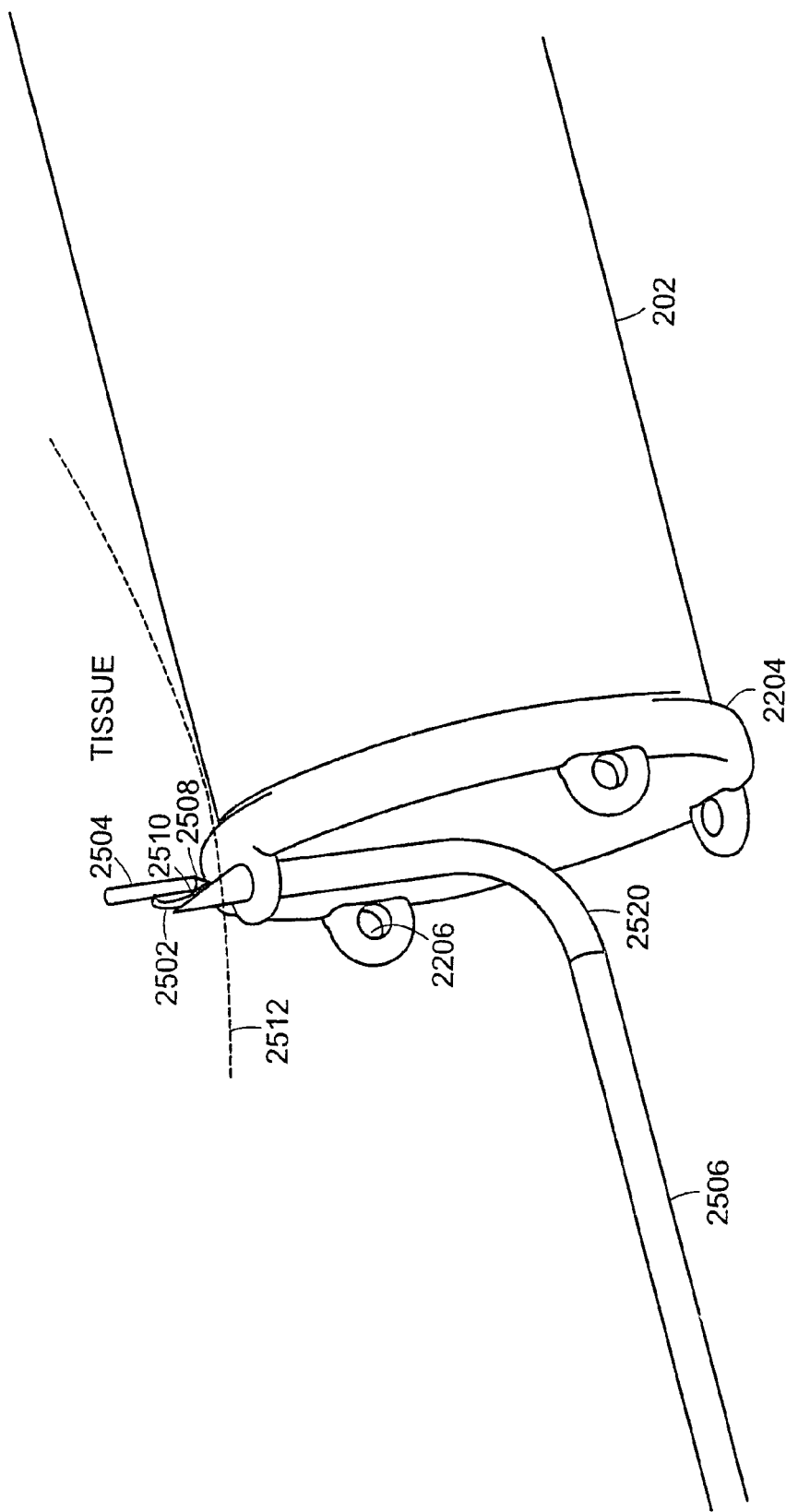
FIG. 25D is a perspective view of the gastrointestinal implant device illustrating the anchor engaged with the tissue.

FIG. 25D is a perspective view illustrating the sharp end 2510 of the needle inserted through an eyelet 2206 for delivery of the anchor 2500 to the tissue 2512. The distal end of the catheter is formed in an arc 2520 to improve access the eyelets 2206. The sharp end 2510 of the catheter is inserted through the eyelet 2206 into the tissue 2516. The anchor pin 2504 of the anchor has been pushed out from the lumen into the tissue 2512.

FIG. 25E is a perspective view illustrating the barb 2508 engaging the tissue 2512 after delivery. The catheter has been removed from the eyelet 2206 leaving the anchor pin 2504 engaging the tissue 2512.

FIGS. 26A-E illustrate an alternative embodiment of a locking mechanism for holding the distal end of the sleeve 202 in position during delivery of the gastrointestinal implant device. A snare wire 2656 is passed through one of the lumens of a catheter 2650 to the distal end. At the distal end, the end of the snare wire 2650 is looped back and attached to or anchored inside the catheter 2650. The folds of the sleeve 202 are advanced through this snare loop. The snare handle 2664 pulls and releases the snare wire 2656 to lock and release the distal end of the sleeve 202. The delivery system includes a pull tap 2666 for releasing a drawstring holding the stent in a collapsed position.

FIG. 26B is cross-sectional view taken along line C-C of FIG. 26A through the inner sheath 2650. The inner sheath has two lumens 2654, 2662 and has a diameter of about 0.078 inches. The first inner lumen 2564 is for passing a guidewire through the inner sheath and is about 0.04 inches in diameter. The second inner lumen 2662 is for passing the snare wire through the inner sheath and is about 0.02 inches in diameter. The end of the snare wire 2658 is anchored inside the inner sheath 2650.

FIG. 26C is a cross-sectional view taken along line DD of FIG. 26A through the outer sheath 2600 showing the inner sheath 2650 within the outer sheath 2600. The outer sheath has a inner diameter of about 0.1 inches and an outer diameter of about 0.143 inches. The open space inside the outer sheath can be used for passing a drawstring through the outer sheath.

FIG. 26D is a cross-sectional view through the distal portion of the catheter 2650 showing the snare capturing the distal end of the sleeve 202. The distal end of the sleeve 202 is captured by the snare wire 2656 by pulling the distal end of the sleeve through a loop formed by the snare wire 2656.

FIG. 26E is a sectional view through the distal portion of the catheter showing the snare locking mechanism. The distal end of the sleeve is locked by pulling the snare wire 2656 in a longitudinal direction 2664 toward the proximal end of the delivery system to capture the sleeve folds against the inner shaft. After the gastrointestinal implant device is properly positioned in the body, the snare wire is advanced in a longitudinal direction 2662 toward the distal end of the delivery system. This opens the snare wire 2656 and releases the sleeve 202.

Figure 27:
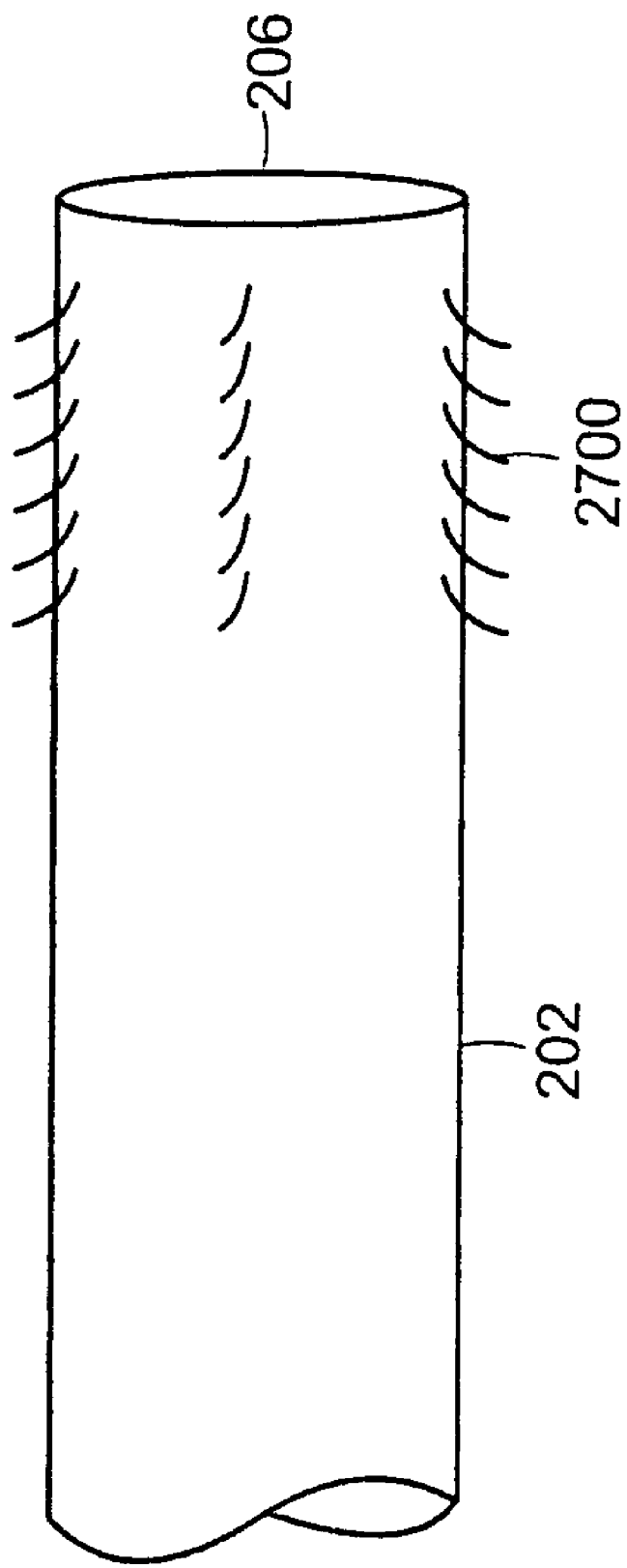
FIG. 27 is a perspective view of the distal portion of the gastrointestinal implant device including texturing at the distal end.

FIG. 27 is a perspective view of the distal portion of the gastrointestinal implant device including texturing 2700. Texturing of the distal end of the sleeve can be added to ensure that the actions of peristalsis do not advance the sleeve proximally, towards the stomach, but keep the sleeve pulled taught in the intestine. At the distal end of the sleeve, texturing 2700 is added with a directional aspect to it. The texturing 2700 can be molded into the sleeve material or added by adhesive or thermal bonding methods. The texturing material contains includes fibril shapes that are directed proximally so that any peristaltic waves that travel proximally, will have less force on the sleeve than distal peristaltic waves.

The gastrointestinal implant device offers a new alternative where other means of weight loss and efforts at behavior modification have failed. Because the gastrointestinal implant device is endoscopically introduced, there is a reduced risk at insertion compared to surgery. The procedure is also completely reversible, making this approach the ideal solution for patients who are desperate to reverse behavioral patterns that have lead to weight gain.

When inserted in the body, the gastrointestinal implant device mimics the duodenal bypass of the Roux-en-Y procedure. The implanted device reduces caloric absorption by delaying enzyme mixing with food and provides the feedback produced by the Roux-en-Y procedure by producing dumping syndrome when high sugar meals are ingested. Rapid stomach emptying is encouraged by inserting a stent in the pylorus to hold the pylorus open and all food bypasses the duodenum and passes rapidly into the jejunum. The implant device is an improvement on the Roux-en-Y procedure because it is minimally invasive and reversible. In the treatment of the super-obese where aggressive weight loss is not achieved, the length of the implant device below the stent can be further increased to drive the patient close to the point of malabsorption.

The gastrointestinal implant device can be used to reduce Type 2 diabetes symptoms by bypassing the duodenum. Following gastric bypass surgery, patients commonly experience complete reversal of Type 2 diabetes. While the exact mechanism of this remarkable effect is not understood, the clinical result is reported in a high percentage of cases. Reversal of Type 2 diabetes after gastric bypass is described in "Potential of Surgery for Curing Type 2 Diabetes Mellitus" by Rubino et al. incorporated herein by reference in its entirety. Since the gastrointestinal implant device provides equivalent blockage of duodenal processes, a similar effect is elicited but without the trauma of surgery. In patients who are not obese but suffer Type 2 diabetes, a modified gastrointestinal implant device is inserted. This gastrointestinal implant device provides the necessary effect to hinder pancreatic processes and receptors without blocking absorption.

In the embodiment of the gastrointestinal implant device for treating diabetes, the length of the stent is selected to allow the pylorus to operate normally. The length of the sleeve is also reduced to mimic the duodenum bypass. The sleeve extends to just below the ligament of Treitz but does not extend further into the jejunum, thus allowing absorption to occur in the jejunum.

While this invention has been particularly shown and described with references to preferred embodiments thereof, it will be understood by those skilled in the art that various changes in form and details may be made therein without departing from the scope of the invention encompassed by the appended claims.

What is claimed is:

1. A delivery system for placing a gastrointestinal implant device in a body comprising:
    a gastrointestinal implant having a flexible sleeve open at both ends;
    an outer sheath adapted for storing a proximal portion of the gastrointestinal implant device;
    an inner sheath within the outer sheath, the inner sheath defining a lumen and extending distally beyond the outer sheath;
    a ball coupled on the distal end of the inner sheath and adapted to guide the delivery system through the alimentary canal; and
    a moveable element moveable within the lumen of the inner sheath and adapted to secure the distal end of the gastrointestinal implant device to the inner sheath during delivery.

2. The delivery system of claim 1, wherein the ball is dimensioned to permit it to be pulled-back through a central lumen of the gastrointestinal implant device.

3. The delivery system of claim 1, further comprising:
    an anchor release mechanism adapted to release an anchor from the outer sheath, the anchor being coupled to the proximal end of the gastrointestinal implant device; and
    a sleeve release mechanism coupled to the moveable element and adapted to release the distal end of a sleeve, the sleeve being coupled at its proximal end to the anchor.

4. The delivery system of claim 3 wherein the anchor release mechanism is adapted to pull the outer sheath toward the proximal end of the delivery system to remove the outer sheath from the anchor.

5. The delivery system of claim 4 wherein the sleeve release mechanism is adapted to pull the moveable element toward the proximal end of the delivery system to release the distal end of the sleeve after the anchor has been released.

6. The delivery system of claim 1 wherein the moveable element is a sleeve retention wire exiting the lumen of the inner sheath and piercing the distal end of the sleeve.

7. The delivery system of claim 1, wherein the gastrointestinal device is adapted for anchoring distal to the pylorus.

8. The delivery system of claim 1, wherein the gastrointestinal device is adapted to be retained within the pyloric orifice.

9. The delivery system of claim 1, wherein the inner sheath defines a second lumen adapted to pass the outer sheath over a guidewire.

10. A delivery system for placing a gastrointestinal implant device in a body comprising:
    a gastrointestinal implant device including a self-expanding anchor for proximally anchoring the device and a sleeve coupled to the anchor;
    an outer sheath adapted to store a proximal portion of the gastrointestinal implant device;
    an inner sheath within the outer sheath, the inner sheath defining a lumen and extending distally beyond the outer sheath;
    a moveable element moveable within the lumen of the inner sheath and adapted to secure the distal end of the sleeve to the inner sheath;
    an anchor release mechanism adapted to release the anchor from the outer sheath; and
    a sleeve release mechanism coupled to the moveable element adapted for releasing the distal end of the sleeve.

11. A delivery system for placing a gastrointestinal implant device in a body comprising:
    an outer sheath to store therewithin a proximal portion of the gastrointestinal implant device, the proximal portion of the gastrointestinal implant device including a self-expanding sleeve anchor to anchor the device, the outer sheath moveable relative to the sleeve anchor to release the sleeve anchor from within the outer sheath;
    an inner sheath within the outer sheath, the inner sheath defining a lumen and extending distal to the outer sheath;
    a moveable element moveable within the lumen of the inner sheath to secure a distal end of a sleeve to the inner sheath, the sleeve coupled at its proximal end to the sleeve anchor;
    a sleeve release mechanism coupled to the moveable element to release the distal end of the sleeve; and
    a ball disposed on the distal portion of the delivery system.

12. The delivery system of claim 11, wherein the moveable element is a sleeve retention wire, which exits the lumen of the inner sheath and pierces the distal end of the sleeve.

13. The delivery system of claim 11, wherein the outer sheath is pulled toward a proximal end of the delivery system to remove the sleeve anchor from the outer sheath.

14. The delivery system of claim 13 wherein the sleeve release mechanism pulls the moveable element toward the proximal end of the delivery system to release the distal end of the sleeve after the sleeve anchor has been released.

15. The delivery system of claim 11, wherein the gastrointestinal device is anchored in the stomach.

16. The delivery system of claim 11, wherein the gastrointestinal device is anchored distal to the pylorus.

17. The delivery system of claim 11, wherein the ball is coupled to the distal end of the inner sheath.

18. The delivery system of claim 11, wherein the ball is dimensioned to permit its retraction through a central lumen of the gastrointestinal implant device.

19. The delivery system of claim 11, wherein the inner sheath defines a second lumen to pass the outer sheath over a guidewire.

20. The delivery system of claim 11, wherein the sleeve anchor comprises a stent.

21. A delivery system for placing a gastrointestinal implant device in a body comprising:
    an outer sheath to store therewithin a proximal portion of the gastrointestinal implant device, the proximal portion of the gastrointestinal implant device including a self-expanding sleeve anchor to anchor the device, the outer sheath moveable relative to the sleeve anchor to release the sleeve anchor from within the outer sheath;
    an inner sheath within the outer sheath, the inner sheath extending distal to the outer sheath toward the distal end of the delivery system, a first lumen within the inner sheath to pass the outer sheath over a guidewire and a second lumen within the inner sheath to move a sleeve retention wire to secure the distal end of a sleeve coupled to the sleeve anchor to the inner sheath by exiting the second lumen of the inner sheath and piercing the distal end of the sleeve;
    a sleeve release mechanism coupled to the moveable element to release the distal end of the sleeve; and
    a ball disposed on the distal portion of the delivery system.

22. The delivery system of claim 21, wherein the outer sheath is pulled toward the proximal end of the delivery system to remove the sleeve anchor from the outer sheath.

23. The delivery system of claim 22, wherein the sleeve release mechanism pulls the moveable element toward the proximal end of the delivery system to release the distal end of the sleeve after the sleeve anchor has been released.

24. A delivery system for placing a gastrointestinal implant device in a body comprising:
    a gastrointestinal implant device comprising a self expanding sleeve anchor and a sleeve coupled at its proximal end to the sleeve anchor;
    an outer sheath storing the self-expanding sleeve anchor in a compressed state within the outer sheath, the outer sheath moveable relative to the sleeve anchor to release the sleeve anchor from within the outer sheath to radially expand;
    an inner sheath within the outer sheath, the inner sheath defining a lumen and extending distal to the outer sheath;
    a moveable element moveable within the lumen of the inner sheath and securing a distal end of the sleeve to the inner sheath;
    a sleeve release mechanism coupled to the moveable element to move the moveable element and thus release the distal end of the sleeve and
    a ball disposed on the distal portion of the delivery system.

25. The delivery system of claim 24, wherein the moveable element is a sleeve retention wire, which exits the lumen of the inner sheath and pierces the distal end of the sleeve.

26. The delivery system of claim 24, wherein the outer sheath is pulled toward a proximal end of the delivery system to remove the sleeve anchor from the outer sheath.

27. The delivery system of claim 26, wherein the sleeve release mechanism pulls the moveable element toward the proximal end of the delivery system to release the distal end of the sleeve after the sleeve anchor has been released.

28. The delivery system of claim 24, wherein the gastrointestinal device is anchored distal to the pylorus.

29. The delivery system of claim 24, wherein the sleeve anchor comprises a stent.

30. The delivery system of claim 24, wherein the ball is coupled to the distal end of the inner sheath.

31. The delivery system of claim 24, wherein the ball is dimensioned to permit its retraction through a central lumen of the gastrointestinal implant device.

32. The delivery system of claim 24, wherein the ball is spherical.

33. The delivery system of claim 11, wherein the ball is spherical.

34. The delivery system of claim 21, wherein the ball is spherical.

* * * * *

UNITED STATES PATENT AND TRADEMARK OFFICE
CERTIFICATE OF CORRECTION

PATENT NO. : 7,758,535 B2  Page 1 of 1
APPLICATION NO. : 12/001365
DATED : July 20, 2010
INVENTOR(S) : Andy H. Levine and Dave Melanson It is certified that error appears in the above-identified patent and that said Letters Patent is hereby corrected as shown below:

On Cover page 1 of the patent, in the first line of item (60) of the Related U.S. Application Data, delete "Continuation-in-part" and insert -- Division --.

In Column 1, line 5, delete "continuation-in-part" and insert -- divisional --.

Signed and Sealed this
First Day of February, 2011

David J. Kappos
*Director of the United States Patent and Trademark Office*